(12) United States Patent
Mash et al.

(10) Patent No.: US 8,637,648 B1
(45) Date of Patent: Jan. 28, 2014

(54) COMPOSITIONS COMPRISING NORIBOGAINE AND AN EXCIPIENT TO FACILITATE TRANSPORT ACROSS THE BLOOD BRAIN BARRIER

(75) Inventors: Deborah C. Mash, Miami, FL (US); Robert M. Moriarty, Michiana Shores, IN (US)

(73) Assignee: Demerx, Inc., Fort Lauderdale, FL (US)

( * ) Notice: Subject to any disclaimer, the term of this patent is extended or adjusted under 35 U.S.C. 154(b) by 0 days.

(21) Appl. No.: 13/165,642

(22) Filed: Jun. 21, 2011

Related U.S. Application Data

(60) Provisional application No. 61/357,485, filed on Jun. 22, 2010, provisional application No. 61/419,773, filed on Dec. 3, 2010.

(51) Int. Cl.
*C07H 19/23* (2006.01)
*C07H 17/02* (2006.01)

(52) U.S. Cl.
CPC ............... *C07H 19/23* (2013.01); *C07H 17/02* (2013.01)
USPC .............. 536/17.4; 514/27; 514/43; 536/27.1

(58) Field of Classification Search
None
See application file for complete search history.

(56) References Cited

U.S. PATENT DOCUMENTS

| | | | |
|---|---|---|---|
| 2,813,873 A | 11/1957 | Janot, et al. |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata, et al. |
| 3,715,361 A | 2/1973 | Epstein, et al. |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,737,586 A | 4/1988 | Potier et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |
| 6,211,360 B1 | 4/2001 | Glick et al. |
| 6,291,675 B1 | 9/2001 | Coop et al. |
| 6,348,456 B1 | 2/2002 | Mash et al. |
| 6,451,806 B2 | 9/2002 | Farrar |
| 6,806,291 B1 | 10/2004 | Sunkel et al. |
| 6,864,271 B2 | 3/2005 | Bazan et al. |
| 7,220,737 B1 | 5/2007 | Mash |
| 7,754,710 B2 | 7/2010 | Mash |
| 8,178,524 B2 | 5/2012 | Mash |
| 2003/0153552 A1 | 8/2003 | Mash et al. |
| 2006/0051317 A1 | 3/2006 | Batrakova et al. |
| 2010/0311722 A1 | 12/2010 | Mash |
| 2010/0311723 A1 | 12/2010 | Mash |
| 2010/0311725 A1 | 12/2010 | Mash |
| 2012/0083485 A1 | 4/2012 | Mash |

FOREIGN PATENT DOCUMENTS

| | | |
|---|---|---|
| CA | 2039197 | 9/1995 |
| DE | 22 17 132 | 10/1972 |
| GB | 0 841 697 | 7/1960 |
| GB | 0 924 042 | 4/1963 |
| GB | 1 256 914 | 12/1971 |
| GB | 1 378 348 | 12/1974 |

(Continued)

OTHER PUBLICATIONS

Yang et al., Expert Opinion on Biological Therapy, 2001, 1(2). 159-175.*
Greenwald et al., Critical Reviews in Therapeutic Drug Carrier System, 2000, 17(2), 101-161.*
U.S. Appl. No. 13/104,406, filed May 10, 2011, Mash et al.
U.S. Appl. No. 13/165,626, filed Jun. 21, 2011, Mash, Deborah C.
U.S. Appl. No. 13/165,639, filed Jun. 21, 2011, Mash et al.
U.S. Appl. No. 13/165,642, filed Jun. 21, 2011, Mash et al.
U.S. Appl. No. 13/198,593, filed Nov. 7, 2011, Mash et al.
U.S. Appl. No. 13/383,405, Moriarty, Robert.
U.S. Appl. No. 13/496,185, Mash, Deborah C.

(Continued)

*Primary Examiner* — Eric S Olson
(74) *Attorney, Agent, or Firm* — Foley & Lardner LLP

(57) ABSTRACT

This invention relates generally to compositions comprising noribogaine and an excipient to facilitate transport across the blood brain barrier.

10 Claims, No Drawings

(56) References Cited

FOREIGN PATENT DOCUMENTS

| GB | 2 271 059 | 4/1994 |
|---|---|---|
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |

OTHER PUBLICATIONS

Ala-Hurula et al. "Erogotamine Abuse: Results of Ergotamine Discontinuation, with Special Reference to the Plasma Concentrations", Cephalalgia, 2/4: abstract only, 1982.
Ala-Hurula et al. "Tolfenamic Acid and Ergotamine Abuse", Headache: The Journal of Head and Face Pain, 21(6): abstract only, 1981.
Alexander. "A Procedure for Drug Screening Without the Need to Transport Urines Use of Ion Exchange Papers and Hem Agglutination Inhibition", Clin Toxicol, 9(3): abstract only, 1976.
Alim et al. "Open-Label, Dose Run-Up Study of Diethylpropion in Initial Cocaine Abstinence", Clinical Neuropharmacology, 17(2): abstract only, 1994.
Almeida. "Use and Abuse of Alcohol and Drugs a Clinical Study of Certain Aspects of Their Interrelationship", Bol of Sanit Panam, 88(1), abstract only, 1980.
Al-Shabanah et al. "Gastric Antiulcer and Cytoprotective Effects of Cathinone, a Psychoactive Alkaloid of Khat (Catha Edulis Forsk.) and Amphetamine in Rats", Regulatory Peptides, abstract only, 1994.
Azevedo et al. "Adrenergic Nerve Degeneration Induced by Condensation Products of Adrenaline and Acetaldehyde", Naunyn-Schmiedeberg's Arch Pharmacol, 300(2): abstract only, 1977.
Bagal et al. "Modulation of Morphine-Induced Antinociception by Ibogaine and Noribogaine", Brain Research, 741(1-2): pp. 258-262, 1996.
Ban. "Adverse Effects to Psychotomimetics. Proposition of a Psychopharmacological Classification", In: Radouco-Thomas S, ed. Pharmacologie, Toxicologie, et abus des psychotomimetiques (hallucinogens)., QV 109: abstract only, 1974.
Bartlett et al. "The Alkaloids of Tabernanthe iboga. Part IV..sup.1 The Structures of Ibogamine, Ibogaine, Tabernanthine and Voacangine", J. Am. Chem. Soc., 80: pp. 126-136, 1958.
Batrakova. "Pluronic P85 Enhances the Delivery of Digoxin to the Brain: In Vitro and In Vivo Studies", The J. of Pharm. and Exp. Thera, 296, p. 551-557, 2001.
Beaubrun. "The Diagnosis and Management of Acute Psychotic Reaction Due to Alcohol and Drugs", Caribb Med J, 36(1): abstract only, 1975.
Beck et al. "Energy-Dependent Reduced Drug Binding as a Mechanism of Vinca Alkaloid Resistance in Human Leukemic Lymphoblasts", Mol Pharmacol, 24(3): abstract only, 1983.
Benet et al. "Pharmacokinetics: Biotransformation of Drugs." In Gilman et al. Goodman and Gilman's the Pharmacological Basis of Therapeutics (1990) :13-16.
Benoist et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunol Immunother, 30(5): abstract only, 1989.
Bert et al. "Non-Amphetaminic Central Stimulation by Alkaloids from the Ibogaine and Vobasine Series", Planta Med., 54(3): abstract only, 1988.
Bhargava et al. "Effects of ibogaine and noribogaine on the antinociceptive action of mu-, delta- and kappa-opioid receptor agonists in mice", Brain Research 752:234-238, 1997.
Blum et al. "Peyote a Potential Ethnopharmacologic Agent for Alcoholism and Other Drug Dependencies Possible Biochemical Rationale", Clin Toxicol, 11(4): abstract only, 1977.
Blum et al. "Possible Role of Tetrahydroisoquinoline Alkaloids in Postalcohol Intoxication States", N Y Acad Sci, 273: abstract only, 1976.
Blum et al. "Putative Role of Isoquinoline Alkaloids in Alcoholism: A Link to Opiates", Alcohol Clin Exp Res, 2(2): abstract only, 1978.
Brady et al. "Analgesic Effects of Intraventricular Morphine and Enkephalins in Nondependent and Morphine-Dependent Rats", J. Pharmacol. Exp. Ther., 222(1): abstract only, 1982.
Buchi et al. "The total synthesis of iboga alkaloids", J. Am. Chem. Soc. vol. 88, p. 3099-3109, 1966.
Bundgaard. "Design of Prodrugs: Bioreversible Derivatives for Various Functional Groups and Chemical Entities." Design of Prodrugs, 1-10, 1985.
Bussel et al. "Isolated Thrombocytopenia in Patients Infected with HIV Treatment with Intravenous Gamma Globulin", Am J Hematol, 28(2): abstract only, 1988.
Caldwell et al. "The Biochemical Pharmacology of Abused Drugs. III. Cannabis, Opiates, and Synthetic Narcotics", Clin. Pharmacol. Ther., 16/6: abstract only, 1974.
Cankat. "Pharmacological Aspects of Drug Induced Headache", Funct. Neurol., 7/6: abstract only, 1992.
Cappendijk et al. "Inhibitory Effects of Ibogaine on Cocaine Self-Administration in Rats", Eur. J. Pharmacol., 241 (2-3): abstract only, 1993.
Cappendijk et al. "The Inhibitory Effect of Norharman on Morphine Withdrawal Syndrome in Rats: Comparisons with Ibogaine", Behavioural Brain Research, pp. 1-3, 1994.
Castle. "Drugs and Fibrotic Reactions—Part I", Adverse Drug React. Bull., 113: abstract only, 1985.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny et al. "Opioid responsiveness of cancer pain syndromes caused by neuropathic or nociceptive mechanisms: a combined analysis of controlled, single-dose studies", Neurobiology 44:857-861, 1994.
Cheze et al. "Determination of ibogaine and noribogaine in biological fluids and hair by LC-MS/MS after Tabernanthe iboga abuse", Forensic Science International, Elsevier Scientific Publishers Ireland Ltd, IE, vol. 176. No. 1, pp. 58-66, 2007.
Criel et al. "Drug Dependent Red Cell Antibodies and Intravascular Haemolysis Occurring in Patients Treated with 9 Hydroxy-Methyl-Ellipticinium", Br J Haematol, 46(4): abstract only, 1980.
Damstrup et al. "Retroperitoneal Fibrosis After Long-Term Daily Use of Ergotamine", Int. Urol. Nephrol., 18/3: abstract only, 1986.
Deecher et al. "Mechanisms of Action of Ibogaine and Harmaline Congeners Based on Radioligand Binding Studies", Brain Research, 571(2): pp. 242-247, 1992.
Diener et al. "Analgesic-Induced Chronic Headache Long-Term Results of Withdrawal Therapy", J Neurol, 236(1): abstract only, 1989.
Dierckx et al. "Intraarterial Sodium Nitroprusside Infusion in the Treatment of Severe Ergotism", Clin. Neuropharmacol., 9/6: abstract only, 1986.
Dzoljic et al. "Effect of Ibogaine on Naloxone-Precipitated Withdrawal Syndrome in Chronic Morphine-Dependent Rats", Arch. Int. Pharmacodyn., 294:64-70, 1988.
Eberwine et al. "Molecular Analysis of Cellular Responses to Opiate Use", Fidia Res. Found. Symp. Ser., 7(Neurotransm. Regul. Gene Transcr.): abstract only, 1991.
Elkind. "Drug Abuse and Headache", Med Clin North Am, 75(3): abstract only, 1991.
Evenson. "Developments in Therapeutic Drug Monitoring and Alkaloid Analysis", Fed Proc, 34(12): abstract only, 1975.
Faglia et al. "Dihydroergocryptine in Management of Microprolactinomas", J Clin Endocrinol Metab, 65(4): abstract only, 1987.

(56) References Cited

OTHER PUBLICATIONS

Fairchild et al. "Keynote Address: Multidrug Resistance: A Pleiotropic Response to Cytotoxic Drugs", Int. J. Radiat. Oncol. Biol. Phys., 20/2: abstract only, 1991.
Finkle. "Phencyclidine Identification by Thin-Layer Chromatography. A Rapid Screening Procedure for Emergency Toxicology", Am. J. Clin. Pathol., 70/2: abstract only, 1978.
Fonne-Pfister et al. "Xenobiotic and Endobiotic Inhibitors of Cytochrome P-450db1 Function, the Target of the Debrisoquine / Sparteine Type Polymorphism", Biochem. Pharmacol., 37(20): abstract only, 1988.
Frances et al. "Effects of Ibogaine on Naloxone-Precipitated Withdrawal in Morphine-Dependent Mice", Fundam Clin Pharmacol, 6(8-9): abstract only, 1992.
Gabr et al. "Changes in Absolute Amount of Alkaloids in Datura-Metel Treated with Certain Growth Regulators", Herba Pol, 21(2): abstract only, 1975.
Garcia et al. "Chronic pain states: pathophysiology and medical therapy", Seminars in Arthritis and Rheumatism, 27:1-16, 1997.
Gennaro. "Remington: The Science and Practice of Pharmacy", Mack Publishing Col., vol. II, pp. 1736 & 1814, 1995.
George et al. "Palliative medicine", Postgrad, Med. Journal, vol. 69, pp. 426-449, 1993.
Gifford et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41(4): abstract only, 1992.
Glick et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657:14-22, 1994.
Glick et al. "Effect of Ibogaine on Acute Signs of Morphine Withdrawal in Rats: Independence from Tremor", Neuropharmacology, 31/5: abstract only, 1992.
Glick et al. "Effects of Aftereffects of Ibogaine on Morphine Self-Administration in Rats", European Journal of Pharmacology, 195(3): abstract only, 1991.
Glick et al. "Ibogaine-like effects of noribogaine in rats", Brain Research, 713:294-297, 1996.
Glick et al. "Local Effects of Ibogaine on Extracellular Levels of Dopamine and Its Metabolites in Nucleus Accumbens and Striatum: Interactions with D-Amphetamine", Brain Research, 628(1-2): abstract, 1993.
Gold et al. "Effect of Methadone Dosage on Clonidine Detoxification Efficacy", Am. J. Psychiatry, 137/3: abstract only, 1980.
Gothoni. "Harmine-, Lon-954- and 5-Hydroxytryptophan-Induced Tremors in Rats Withdrawn from Ethanol", Acta Pharmacol Toxicol, 57(1): abstract only, 1985.
Gross. "Effect of Ergot Alkaloids on Serum Prolactin in Non-Psychotic Organic Brain Syndrome of the Elderly", Exp Aging Res, 5(4): abstract only, 1979.
Gunn. "Relations Between Chemical Constitution, Pharmacological Actions, and Therapeutic Uses, in the Harmine Group of Alkaloids", From the Pharmacological Laboratory, University of Oxford:379-396, 1935.
Haber et al. "Tetrahydroisoquinolines—Endogenous Products After Chronic Alcohol Abuse", Pharmazie, 47/1: abstract only, 1992.
Halikas et al. "Treatment of Crack Cocaine Use with Carbamazepine", Am J Drug Alcohol Abuse, 18(1): abstract only, 1992.
Hanks. "Opioid-responsive and opioid-non-responsive pain in cancer", British Medical Bulletin 47:718-731, 1991.
Hardman et al. "Goodman & Gilman's The Parmacological Basis of Therapeutics" (9th ed, 1996) p. 51 and 57-58.
Harsing, Jr. et al. "Evidence that Ibogaine Releases Dopamine from the Cytoplasmic Pool in Isloated Mouse Striatum", Journal of Neural Transmission General Section, 96(3): abstract only, 1994.

Hearn et al. "Identification and Quantitation of Ibogaine and an o-Demethylated Metabolite in Brain and Biological Fluids Using Gas Chromatography-Mass Spectrometry." J. Analytical Toxicology, 19:427-434, 1995.
Heel et al. "Buprenorphine: A Review of Its Pharmacological Properties and Therapeutic Efficacy", Drugs, 17(2): abstract only, 1979.
Henry et al. "Reversible Cerebral Arteriopathy Associated with the Administration of Ergot Derivatives", Cephalalgia, 4/3: abstract only, 1984.
Ho et al. "Metabolism of Harmaline in Rats." Biochemical Pharmacology, 20:1313-1319, 1971.
Hoes. "Clinical Criteria for the Selection of Anxiolytics", Tijdschr. Ther. Geneesm. Onderz., 9/9: abstract only, 1984.
Holbrook. "Nicotine Addiction." In Isselbacher et al. Harrison's Principles of Internal Medicine:2433-2437, 1994.
Holzner et al. "The Neuroleptic Sleeping Course in Chronic Headache", Therapiewoche, 35/36: abstract only, 1985.
Huang et al. "Cytotoxicity and Sister Chromatid Exchanges Induced in Vitro by Six Anticancer Drugs Developed in the People's Republic of China", J Natl Cancer Inst, 71(4): abstract only, 1983.
Hubens et al. "Chronic Intake of a Hydrogenated Ergot Alkaloid Causing Peripheral Vascular Ischemia—A Case Report", Vasc. Surg., 21/4: abstract only, 1987.
Huffman et al. "A Formal Synthesis of (±)-Ibogamine", J. Org. Chem. vol. 50, pp. 1460-1464, 1985.
Isler. "Treatment of Headache", Schweiz. Med. Wochenschr., 114/35: abstract only, 1984.
Jaffe. "Drug Addiction and Drug Abuse." In Gilman et al. Goodman and Gilman's The Pharmacological Basis of Therpeutics:522-523, 559-568, 1990.
Jaffe. "Psychopharmacology and Opiate Dependence", U.S. Public Health Serv. Publ., 1957-1967:1836, 1967.
James, "Linkers for solid phase organic synthesis", Tetrahedron 55, 4855-4946, 1999.
Jane et al. "High-Performance Liquid Chromatographic Analysis of Basic Drugs on Silica Columns Using Non-Aqueous Ionic Eluents. II. Application of UV, Fluorescence and Electrochemical Oxidation detection", J. Chromatogr., 323(2): abstract only, 1985.
Jansen et al. "Ethnopharmacology of Kratom and the Mitragyna Alkaloids", J Ethnopharmacol, 23(1): abstract only, 1988.
Janzen. "History of Use of Psychotropic Drugs in Central Africa", Psychotropes, 1/2: abstract only, 1983.
Justins. "Management strategies for chronic pain", Annals of the Rheumatic Diseases, vol. 55, pp. 588-596, 1996.
Kalix. "Khat: A Plant with Amphetamine Effects", J Subst Abuse Treat, 5(3): abstract only, 1988.
Kalix. "Pharmacological Properties of the Stimulant Khat", Pharmacol. Ther., 48/3: abstract only, 1990.
Keefner. "A Gas Chromatography-Mass Spectrometry (GCMS) Method for Ibogaine", Society for Neuroscience Abstracts, 19(1-3): abstract only, 1993.
Keller et al. "Modulation of Neopterin Release by Human Kupffer Cells in Culture: Possible Implication in Clinical Monitoring of HIV-Seropositive Subjects", Cells Hepatic Sinusoid, 3: abstract only, 1991.
Knoll. "Azidomorphines and Homopyrimidazols: A New Approach to the Ideal Analgetic", Acta Physicol Pharmacol Bulg, 3(2): abstract only, 1977.
Knoll. "Azidomorphines: A New Family of Potent Analgesics with Low Dependence Capacity", Prog. Neuro-Psychopharmacol., 3/1-3: abstract only, 1979.
Koch et al. "Drug-Induced Liver Injury in Liver Biopsies of the Years 1981 and 1983, their Prevalence and Type of Presentation", Path. Res. Pract., 179: abstract only, 1985.
Konig. "Psychiatric Intensive Therapy After Acute Alkaloid Withdrawal Syndrome", Infusionsther Klin Ernahr, 6(1): abstract only, 1979.
Kornetsky, "Pharmacology Drugs Affecting Behavior", New York, John Wiley & Sons, pp. 186-187, 1976.
Kostowski et al. "The Effects of Some Hallucinogens on Aggressiveness of Mice and Rats" Pharmacology vol. 7, pp. 259-263, 1972.

(56) References Cited

OTHER PUBLICATIONS

Krug. "Cocaine Abuse: Historical, Epidemiologic, and Clinical Perspectives for Pediatricians", Advances in Pediatrics, 36:369-406, 1989.
Kupers et al., "Morphine differentially affects the sensory and affective pain ratings in neuorgenic and idiopathic forms of pain." Pain 47:5-12, 1991.
Lakoski et al. "Electrophysiologic Characterization of an Ibogaine Metabolite in Dorsal Raphe Nucleus and Hippocampus." Soc. Neurosc. 21:716 Abstract only, 1995.
Larson-Prior et al. "Electrophysiologic Characterization of an Ibogaine Metabolite in the Cerebellar Cortex." Soc. Neurosc. 21:716 Abstract only, 1995.
Lemontt et al. "Increase MDR Gene Expression and Decreased Drug Accumulation in Multidrug-Resistant Human Melanoma Cells", Cancer Res, 48(22): abstract only, 1988.
Leoni et al. "Effect of Cocaine and Morphine on Neutral Endopeptidase Activity of Human Peripheral Blood Mononuclear Cells Cultures with Lectins", Cell Biochem Funct, 11(3): abstract only, 1993.
Lerida et al. "Incidence of Morphine Withdrawal and Quasi-Abstinence Syndrome in a Model of Chronic Pain in the Rat", Neurosci., 81(1-2): abstract only, 1987.
Lewis et al. "Adverse Reactions and Interactions with .beta.-Adrenoceptor Blocking Drugs", Med. Toxicol., 1/5: abstract only, 1986.
Lewis et al. "Narcotic Analgesics and Antagonists", Annu Rev Pharmacol, 11: abstract only, 1971.
Licht et al. "Induction of Multiple-Drug Resistance During Anti-Neoplastic Chemotherapy In-Vitro", Int J Cancer, 49(4): abstract only, 1991.
Ling et al., "Drugs of Abuse-Opiates", in Addtiction Medicine [Special Issue], Western Journal of Medicine, 152:565-572, 1990.
Low et al. "Effects of Acronycine and Cytouchalasin B on the Division of Rat Leukemia Cells", Exp Cell Res, 131(1): abstract only, 1981.
Ma et al. "Inhibition of Respiratory Burst Activity in Alveolar Macrophages by Bisbenzylisoquinoline Alkaloids: Characterization of Drug-Cell Interaction", Exp. Lung Res., 18/6: abstract only, 1992.
Maisonneuve et al. "Interactions of Ibogaine and D-Amphetamine: in vivio Microdialysis and Motor Behavior in Rats." Brain Research 579:87-92, 1992.
Maisonneuve et al. "Acute and Prolonged Effects of Ibogaine on Brain Dopamine Metabolism and Morphine-Induced Locomotor Activity in Rats", Brain Research, 575(1): abstract only, 1992.
Maisonneuve et al. "Interactions Between Ibogaine, a Potential Anti-Addictive Agent, and Morphine: an in Vivo Microdialysis Study", Eur. J. Pharmacol., 199(1): abstract only, 1991.
Martellotta et al. "Effects of the Calcium Antagonist Isradipine on Cocaine Intravenous Self-Administration in Rats", Psychopharmacologia, 113(3-4): Abstract only, 1994.
Martin et al. "Neuropathic Pain in Cancer Patients: Mechanisms, Syndromes, and Clinical Controversies," Journal of Pain and Symptom Management 14(2):99-117, 1997.
Mash et al, "Properties of Ibogaine and its Principle Metabolite (12-hydroxyibogamine) at the MK-801 binding site of the NMDA receptor complex," Neuroscience Letters, 192, 53-56, 1995.
Mash et al. "Ligand Binding Profiles of Ibogaine and its O-demethylated Metabolite Noribogaine: Implications for Developing Novel Multi-target Anti-addiction Agents." Soc. Neurosc. (1995) 21:717 Abstract only.
Mash et al. "Preclinical screening of an ibogaie metabolite (noribogaine) on cocaine-induced hyperlocomotion and cocaine self-administration." Soc. Neurosc. 22:1929 Abstract only, 1996.
Mash et al. "Ibogaine in the Treatment of Heroin Withdrawal," The Alkaloids 56:1-17, 2001.
Mateer et al. "Reversible Ipecac Myopathy", Arch. Neurol., 42/2: abstract only, 1985.
Matharu et al. "Preformulation and Development of Ibogaine Injection for the Treatment of Drug Abuse", Pharmaceutical Research, 10: abstract only, 1993.
Mattingly et al. "Selective Antagonism of Dopamine D Sub1 and D Sub 2 Receptors Does Not Block the Development of Behavioral Sensitization to Cocaine", Psychopharmacologia, 114(2): abstract only, 1994.
McNeish et al. "The 5-HT Sub 3 Antagonist Zacopride Attenuates Cocaine-Induced Increases in Extracellular Dopamine in Rat Nucleus Accumbens", Pharmacology, Biochemistry, and Behavior, 45(4): abstract only, 1993.
Melchior et al. "Preference for Alcohol Evoked by Tetra Hydro Papaveroline Chronically Infused in the Cerebral Ventricle of the Rat", Pharmacol Biochem Behav, 7(1): abstract only, 1977.
Mendelson et al. "Cocaine and Other Commonly Abused Drugs." In Isselbacher et al. Harrison's Principles of Internal Medicine:2429-2433, 1994.
Menzies et al. "Gangrene of the Small Bowel: A Complication of Methysergide Therapy", Aust. N. Z. J. Surg., 52/5: abstract only, 1982.
Metelitsa. "Pharmacological Agents in Controlling Smoking", Biull Vsesoiuznogo Kardiol Nauchn Tsentra, 10(1): abstract only, 1987.
Millan, "k-Opioid Receptors and Analgesia," Trendes in Pharmacologicla Sciences, 11, pp. 70-76, 1990.
Mizuhashi et al. "Antitumor Activities of IKP-104 A 4-1H Pyridizinone Derivative on Cultured and Implanted Tumors", Jpn J Cancer Res, 81(12): abstract only, 1990.
Montefiori et al. "In Vitro Evaluation of Mismatched Double-Stranded RNA (Ampligen) for Combination Therapy in the Treatment of Acquired Immunodeficiency Syndrome", AIDS Res Hum Retroviruses, 5(2): abstract only, 1989.
Mulamba et al., Alcaloides de Tabernanthe Pubescens. Journal of Natural Products, vol. 44, No. 2, p. 184-189, 1981.
Nishiyama et al. "Expression of the Multidrug Transporter, P-Glycoproteiin, in Renal and Transitional Cell Carcinomas", Cancer, 71(11):3611-3619, 1993.
Nooter et al. "Multidrug Resistance (MDR) Genes in Haematological Malignancies", Cytotechnology, 12(1-3): abstract only, 1993.
Nunn-Thompson et al. "Pharmacotherapy for Making Cessation", Clin Pharm, 8(10): abstract only, 1989.
Obach et al., "Cythochrome P4502D6 Catalyzes the O-Demethylation of the Psychoactive Alkaloid Ibogaine to 12-Hydroxyibogamine" Drug Metabolism and Disposition 26(8):764-768, 1998.
O'Hearn et al. "Degenration of Prukinje Cells in Parasagittal Zones of the Cerebellar Vermis After Treatment with Ibogaine of Harmaline", Neuroscience, 55(2): abstract only, 1993.
O'Hearn et al. "Ibogaine Induces Glial Activation in Parasagittal Zones of the Cerebellum", Neuroreport, 4/3: abstract only, 1993.
Pablo et al, "Noribogaine Stimulates Naloxone-Sensitive[35S]GTPgammaS Binding," NeuroReport, 9, pp. 109-114. (Website Publication Date of Dec. 20, 1997.), 1998.
Pacifici et al. "Immunological Effect of Cocaine and Host Resistance in Mice", Int J Immunother, 8(2): abstract only, 1992.
Palyi. "Survivial Responses to New Cytostatic Hexitols of P388 Mouse and K562 Leukemia Cells in Vitro", Cancer Treat. Rep., 70(2): abstract only, 1986.
Pantazis et al. "Efficacy of Camptothecin Congeners in the Treatment of Human Breast Carcinoma Xenografts", Oncology Research, 5(8): abstract only, 1994.
Pehek. "Effects of Cathinone and Amphetamine on the Neurochemistry of Dopamine in Vivo", Neuropharmacology, 29/12: abstract only, 1990.
Perera et al. "Tertiary Indole Alkaloids of *Tabernaemontana dichotoma* Seeds", Planta Med., 49/1: abstract only, 1983.
Perrin. "Clinical Pharmacokinetics of Ergotamine in Migraine and Cluster Headache", Clin. Pharmacokin., 10/4: abstract only, 1985.
Popik et al. "NMDA Antagonist Properties of the pUtative Antiaddictive Drug, Ibogaine", Journal of Pharmaceutical and Experimental Therapeutics, 275(2), 753-760, 1995.
Popik et al. "The Putative Anti-Addictive Drug Ibogaine is a Competitive Inhibitor of ( SUP 3 H) Binding to the NMDA Receptor Complex", Psychopharmacologia, 114(4): abstract only, 1994.

(56) References Cited

OTHER PUBLICATIONS

Popik et al. "100 Years of Ibogaine: Neurochemical and Pharmacological Actions of a Putative anti-addictive Drug", Pharmacological Reviews 47(2), pp. 235-253, 1995.
Pulvirenti et al. "Lisuride Reduces Intravenous Cocaine Self-Administration in Rats", Pharmacology, Biochemistry and Behavior, 47(4): abstract only, 1994.
Qiu et al. "The Influence of Chronic Nicotine Treatment on Stress-Induces Gastric Ulceration and Emptying Rate in Rats", Experientia, 48(4): abstract only, 1992.
Rezvani et al. "Noribogaine, a Primary Ibogaine Metabolite, Reduces Alcohol Intake in P and Fawn-Hooded Rats." RSA Annual Scientific Meeting Abstract only, 1995.
Rezvani et al. "Reduction of Alcohol Intake in Alcohol Preferring Fawn-hooded and P Rats by Noribogaine, the Primary Metabolite of Ibogaine." NIDA Monograph Series (1996) 162:281 Abstract only.
Ricceri et al. "Postnatal cocaine Esposure Affects Neonatal Passive Avoidance Performance and Cholinergic Development in Rats", Pharmacology, Biochemistry and Behavior, 45(2): abstract only, 1993.
Rodriguez et al. "Cocaine Adminstration Prior to Reactivation Facilitates Later Acquisition of an Avoidance Response in Rats", Psychopharmacologia, 112(2-3): abstract only, 1993.
Rosenmund et al. "Ibogamin, Ibogain and Epiibogamin" Chem. Ber. vol. 108, p. 1871-1895, 1975. structures and abstract only.
Sachs et al. "Corneal Complications Associated with the Use of Crack Cocaine", Ophthalmology, 100(2): abstract only, 1993.
Salmoiraghi et al. "Effects of LSD 25, BOL 148, Bufotenine, Mescaline and Ibogaine on the Potentiation of Hexobarbital Hypnosis Produced by Serotonin and Reserpine." J. Pharm and Exp Ther. vol. 120. No. 1, pp. 20-25, 1957.
Samadi-Baboli et al. "Preparation of Low Density Lipoprotein-9-Methoxy-Illipticin Complex and Its Cytotoxic Effect Against L1210 and P 388 Leukemic Cells in Vitro", Eur J Cancer Clin Oncol, 25(2): abstract only, 1989.
Saper et al. "Ergotamine Tartrate Dependency: Features and Possible Mechanisms", Clin. Neuropharmacol., 9/3: abstract only, 1986.
Schecter et al. "Comparison of the Behavioral Effects of Ibogaine from Three Sources: Mediation of Discriminative Activity", European Jornal of Pharmacology, 249(1): abstract only, 1993.
Schneider et al. "Analysis of the Cardiovascular Action of Ibogaine Hydrochloride (1)" Arch. Int. Pharmacodyn. vol. 110, pp. 92-102, 1957.
Schneider et al., Neuropharmacological Studies of Ibogaine: An Indole Alkaloid with Central Stimulant Properties' Ann. of N.Y. Acad. Sci. vol. 66, pp. 765-776, 1957.
Schneider et al., "Potentiation Action of Ibogaine on Morphine Analgesia" Experiential vol. 12, pp. 323-324, 1956.
Schnider et al. "Use and Abuse of Analgesics in Tension-Type Headache", Cephalalgia, 14/2: abstract only, 1994.
Schuckit et al. "Opioid Drug Use." In Isselbacher et al. Harrison's Principles of Internal Medicine :2425-2429, 1994.
Schuckit. "Alcohol and Alcoholism." In Isselbacher et al. Harrison's Principles of Internal Medicine :2420-2425, 1994.
Seeber et al. "In Vivo Resistance Towards Anthracyclines, Etoposide, and Cis-Diamminedichloroplatinum (II)", Cancer Res., 42(11): abstract only, 1982.
Sehested et al. "The Carboxylic Ionophore Monensin Inhibits Active Drug Efflux and Modulates In-Vitro Resistance in Daunorubicin Resistant Enrlich Ascites Tumor Cells", Biochem Pharmacol, 37(17): abstract only, 1988.
Sershen et al. "Ibogaine Antagonizes Cocaine-Induced Locomotor Stimulation in Mice", Life Sci., 50(15): abstract only, 1992.
Sershen et al. "Ibogaine Reduces Amphetamine-Induced Locomotor Stimulation in C57BL/6By Mice, but Stimulates Locomotor Activity in Rats", Life Sci., 51(13): abstract only, 1992.
Sershen et al. "Ibogaine Reduces Preference for Cocaine Consumption in C57BL/6By Mice", Pharmacol., Biochem. Behav., 47(1): abstract only, 1994.

Shen et al. "Antagonists at Excitatory Opioid Receptors on Sensory Neurons in Culture Increase Potency and Specificity of Opiate Analgesics and Attenuate Development of Tolerance / Dependence", Brain Research, 636(2): abstract only, 1994.
Sheppard. "A Preliminary Investigation of Ibogaine: Case Reports and Recommendations for Further Study", J. Subst. Abuse Treat., 11/4: abstract only, 1994.
Shir et al., "Neuropathic pain unrelieved by morphine, alleviated by haloperidol" Harefuah 118(8):452-454, Abstract only, 1990.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula et al. "Rationale for Design for Biologically Reversible Drug Derivatives: Prodrugs." Journal of Pharmaceutical Sciences, 64(2):181-210, 1975.
Slotkin et al. "A Model of Harmine Metabolism in the Rat." The Journal of Pharmacology and Experimental Therapeutics, 174(3):456-462, 1970.
Slotkin et al. "Blood Levels and Urinary Excretion of Harmine and its Metabolites in Man and Rats." The Journal of Pharmacology and Experimental Therapeutics, 173(1):26-30, 1970.
Slotkin et al. "Urinary Metabolites of Harmine in the Rat and their Inhibition of Monoamine Oxidase." Biochemical Pharmacology 19:125-131, 1970.
Sloviter et al. "A Common Mechanism of Lysergic Acid, Indolealkylamine and Phenethylamine Hallucinogens: Serotonergic Mediation of Behavioral Effects in Rats" J. Pharm. Exp. Ther. vol. 214, No. 2, pp. 231-238, 1980.
Smith. "Interaction of Biogenic Amines with Ethanol", Adv Exp Med Biol, 56: abstract only, 1975.
Solinas et al. "Solid-supported reagents and catch-and-release techniques in organic synthesis". Synthesis 20070816 DE LNKD-DOI:10.1055/S-2007-983806, No. 16., pp. 2409-2453, 2007.
Stella. "Pro-drugs: An Overview and Definition." Prodrugs As Novel Drug Delivery System. ACS Symposium Series :1-115, 1975.
Stella. "Pro-drugs as Novel Drug Delivery Systems", Higuchi, T. et al., ed. (American Chemical Society, Washington), pp. 1-49, 1975.
Sugiyama et al. "Quantitative Analysis of Cell-Kill Effects of Anticancer Drugs: Consideration of Both In Vitro and In Vivo Expreimental Systems", Gan To Kagaku Ryoho, 14(12): abstract only, 1987.
Tarnower et al. "Ergotism Masquerading as Arteritis", Postgrad Med, 85(1): abstract only, 1989.
Teoh et al. "Buprenorphine Effects on Morphine- and Cocaine-Induced Subjective Responses by Drug-Dependent Men", Journal of Clinical Psychopharmacology, 14(1): abstract only, 1994.
Tfelt-Hansen et al. "Nitroglycerin for Ergotism. Experimental Studies in Vitro and in Migraine Patients and Treatment of an Overt Case", Eur. J. Clin. Pharmacol., 22/2: abstract only, 1982.
Torrenegra et al. "Alkaloids of *Stemmadenia* grandiflora", Phytochemistry, 27(6): pp. 1843-1848, 1988.
Tsuruo. "Multidrug Resistance: A Transport System of Antitumor Agents and Xenobiotics", Princess Takamatsu Symp, 21: abstract only, 1990.
Uldry et al. "Cerebrovascular Accidents in Relation to Drug Consumption or Drug Abuse", Schweiz Rundsch Med Prax, 78(23): abstract only, 1989.
Valadez et al. "Persistence of the Ability of Amphetamine Preexposure to Facilitate Acquistion of Cocaine Self-Administration", Pharmacology, Biochemistry and Behavior, 47(1): abstract only, 1994.
Valencia et al. "Obovatine, a new bisindole alkaloid from stemmadenia obovata", Journal of Natural Products, 58(1):pp. 134-137, 1995.
Vescovi et al. "Successful Treatment of Opiate Withdrawal Using Lysine Acetylsalicylate", Curr. Ther. Res., Clin. Exp., 33/5: abstract only, 1983.
Villalba et al. "Uses and Abuses of Ipecacuana Syrup", Farm. Clin., 9/1: abstract only, 1992.
Wells et al. "Recognition and Treatment of Arterial Insufficiency from Cafergot", J. Vasc. Surg., 4/1: abstract only, 1986.

(56) References Cited

OTHER PUBLICATIONS

Whitaker et al. "High Affinity 3H-Serotonin Binding to Caudate: Inhibition by Hallucinogenic and Serotonergic Drugs", Psychopharmacology, vol. 59, pp. 1-5, 1978.
Whitaker et al., "Selective Labeling of Serotonin Receptors by d'(3H)Lysergic Acid Diethylamide in Calf Caudate", Proc. Natl. Acad. Sci., USA vol. 75, No. 12, pp. 5783-5787, 1978.
Whittaker et al. "Recurrent Laryngeal Nerve Paralysis in Patients Receiving Vincristine and Vinblastine", Br Med J, 1(6071): abstract only, 1977.
Widler et al. "Pharmacodynamics and Pharmacokinetics of Khat: a Controlled Study", Clin. Pharmacol. Ther., 55/5: abstract only, 1994.
Wildmann. "Heterocycles as Physiological Ligands for the Benzodiazepine Receptor and for Other Binding Sites", Pharmacol Res, 21(6): abstract only, 1989.
Williams, Jr. et al. "The 'Alice in Wonderland' Experience Ergot Alkaloid Therapy for Prolactin-Secreting Pituitary Tumors", West. J. Med., 138/3: abstract only, 1983.
Wishart et al. "Is Multidrug Resistance Relevant in Breast Cancer", Eur. J. Surg. Oncol., 17/5: abstract only, 1991.
Witt et al. "Pharmacodynamic and Pharmacokinetic Characterization of Poly(Ethylene glycol) Conjugation to Met-Enkephalin Analog [$_D$-Pen$^2$,$_D$-Pen$^5$]-enkephalin (DPDPE)", J. of Pharm. and Exp. Thera., 298(2), pp. 848-856, 2001.
Witt et al. "Pluronic P85 Block Copolymer Enhances Opioid Pepetide Analgesia", J. of Pharm. and Exp. Thera., 303(2), pp. 760-767, 2002.
Worz. "Effects and Risks of Psychotropic and Analgesic Combinations", Am. J. Med., 75/5A: abstract only, 1983.
Zetler et al. "Pharmacokinetics in the Rat of the Hallucinogenic Alkaloids Harmine and Harmaline." Naunyn-Schmiedeberg's Arch. Pharmacol., 285, 273-292, 1974.
Zetler et al. "Cerebral Pharmacokinetics of Tremor-Producing Harmala and Iboga Alkaloids" Pharmacology vol. 7, No. 4, pp. 237-248, 1972.
International Search Report and Written Opinion dated Oct. 4, 2012 in related PCT Application Serial No. PCT/US2012/022255.
International Search Report for PCT/US2011/045081 dated Oct. 4, 2011.
Mulamba et al., "Alkaloids from tabernanthe pubescens", Journal of Natural Products, (1981) 44(2):184-189.

\* cited by examiner

COMPOSITIONS COMPRISING NORIBOGAINE AND AN EXCIPIENT TO FACILITATE TRANSPORT ACROSS THE BLOOD BRAIN BARRIER

CROSS-REFERENCE TO RELATED APPLICATIONS

This application claims priority under 35 U.S.C. §119(e) to U.S. Provisional Patent Application Ser. No. 61/357,485, filed on Jun. 22, 2010, and to U.S. Provisional Patent Application Ser. No. 61/419,773, filed on Dec. 3, 2010, both of which applications are incorporated by reference herein in their entirety.

FIELD OF THE INVENTION

This invention relates generally to compositions comprising noribogaine and an excipient to facilitate transport across the blood brain barrier.

STATE OF THE ART

Noribogaine is a well known derivative of ibogaine and is sometimes referred to as 12-hydroxyibogaine. It is a metabolite of ibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tyrptamine, tetrahydrohavaine and indolazepines. Noribogaine can be depicted by the following Formula:

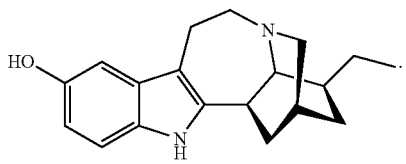

Noribogaine and its pharmaceutically acceptable salts have recently received significant attention as non-addictive alkaloids useful in treating drug dependency (U.S. Pat. No. 6,348,456) and as a potent analgesic (U.S. Pat. No. 7,220,737).

Noribogaine is typically administered orally or intravenously and becomes systemically available to the treated patient. While noribogaine allosterically binds tightly to the μ and κ receptors, the systemic circulation of noribogaine increases the likelihood of undesirable side effects while the availability of noribogaine is limited by the efficiency of its passage across the blood brain barrier.

Accordingly, there is a need to reduce the systemic circulation of noribogaine while maintaining or increasing its concentration in the brain particularly at the μ and κ receptors.

SUMMARY OF THE INVENTION

This invention relates to increased cranial delivery of noribogaine by use of a pharmaceutically acceptable excipient to enhance blood brain barrier penetration. It is contemplated that the excipient cooperatively increases the concentration of noribogaine in the brain of the treated patient thereby reducing the systemic concentration of noribogaine in the remainder of the patient's body. While not all drugs react cooperatively with blood brain barrier excipients, it is contemplated that noribogaine will show a significant increase in cranial concentration when used in conjunction with such an excipient. It is further contemplated that in view of such targeted delivery, the amount of noribogaine required to effect therapy will be reduced.

Accordingly, in one of its composition aspects, this invention is directed to a pharmaceutical composition comprising a therapeutically effective amount of noribogaine, or a derivative or pharmaceutically acceptable salt thereof, and an effective amount of a pharmaceutically acceptable excipient to enhance the blood brain barrier penetration of noribogaine.

In some embodiments, the excipient which enhances the blood brain barrier penetration of noribogaine is a biocompatible dehydrating saccharide such as mannitol.

In some embodiments, at least a portion of the mannitol or other dehydrating saccharide is bound to the noribogaine via a biocompatible, cleavable linking group. It is contemplated that such compounds will reduce the concentration of the saccharide necessary to enhance the blood brain barrier penetration of noribogaine. In one such embodiment, there is provided a compound of Formula I:

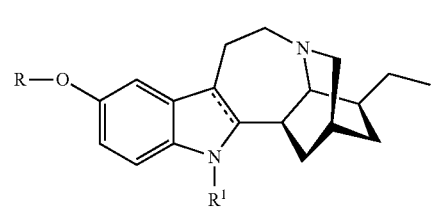

wherein
= is a single or double bond;
R is hydrogen, alkyl, —C(O)-alkyl, or the group -L-S where L is a covalent bond or is a biocompatible, cleavable linking group and S is a dehydrating saccharide or oligosaccharide;
$R^1$ is hydrogen or the group -L-S where L is a covalent bond or is a biocompatible, cleavable linking group and S is a dehydrating saccharide or oligosaccharide; provided that at least one of R and $R^1$ is -L-S;
or a pharmaceutically acceptable salt thereof.

In another of its composition aspects, there is provided a compound of Formula I or its pharmaceutically acceptable salt.

In some embodiments, R is hydrogen and $R^1$ is -L-S. In some embodiments, R is —C(O)-alkyl and $R^1$ is -L-S. In some embodiments, R is -L-S and $R^1$ is hydrogen. In some embodiments, both R and $R^1$ are -L-S.

In another of its composition aspects, this invention is directed to a pharmaceutical composition comprising a pharmaceutically acceptable excipient and a therapeutically acceptable amount of a compound of Formula I above.

In some embodiments, R is hydrogen and $R^1$ is -L-S. In some embodiments, R is -L-S and $R^1$ is hydrogen. In some embodiments, R is —C(O)-alkyl and $R^1$ is -L-S. In some embodiments, both R and $R^1$ are -L-S. In some embodiments, the pharmaceutically acceptable excipient comprises mannitol.

In one of its method aspects, there is provided a method for treating pain in a patient which method comprises administering to said patient a pharmaceutical composition comprising a therapeutically effective amount of noribogaine or a pharmaceutically acceptable salt thereof and an effective amount of a pharmaceutically acceptable excipient to enhance the blood brain barrier penetration of noribogaine.

In another of its method aspects, there is provided a method for treating addiction in a patient which method comprises administering to said patient a pharmaceutical composition comprising a therapeutically effective amount of noribogaine or a pharmaceutically acceptable salt thereof and an effective amount of a pharmaceutically acceptable excipient to enhance the blood brain barrier penetration of noribogaine.

In one of its method aspects, there is provided a method for treating pain in a patient which method comprises administering to said patient a therapeutically effective amount of a compound of Formula I or a pharmaceutical composition comprising a therapeutically effective amount of a compound of Formula I and a pharmaceutically acceptable excipient.

In another of its method aspects, there is provided a method for treating addiction in a patient which method comprises administering to said patient a therapeutically effective amount of a compound of Formula I or a pharmaceutical composition comprising a therapeutically effective amount of a compound of Formula I and a pharmaceutically acceptable excipient.

DETAILED DESCRIPTION

This invention is directed to compositions comprising noribogaine, or a derivative or pharmaceutically acceptable salt thereof, and an excipient to facilitate transport across the blood brain barrier.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients.

1. DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of when used to define compositions and methods, shall mean excluding other elements of" any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to compositions comprising noribogaine, or a derivative or pharmaceutically acceptable salt thereof, and an excipient to facilitate transport across the blood brain barrier.

As used herein, the term "noribogaine" refers to the compound:

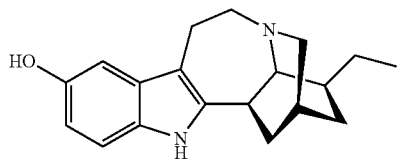

as well as its pharmaceutically acceptable salts thereof. Conventionally, noribogaine is prepared by demethylation of naturally occurring ibogaine:

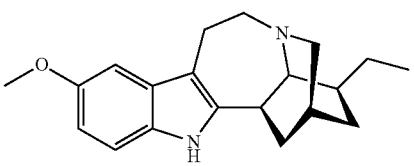

which is isolated from *Tabernanthe iboga*, a shrub of West Africa. Demethylation may be accomplished by conventional techniques such as by reaction with boron tribromide/methylene chloride at room temperature followed by conventional purification. (See, for example, Huffman, et al., J. Org. Chem. 50:1460 (1985)). Methods for the synthesis and purification of noribogaine are disclosed in U.S. patent application Ser. No. 13/104,406, entitled Methods and Compositions for Preparing and Purifying Noribogaine, filed on May 10, 2011, which is hereby incorporated by reference in its entirety. This invention is not limited to any particular chemical form of noribogaine and the drug may be given to patients either as a free base or as a pharmaceutically acceptable addition salt.

As used herein, the terms "blood-brain barrier" or "BBB" refer to the barrier between the peripheral circulation and the brain and spinal cord which is formed by tight junctions within the brain capillary endothelial plasma membranes, creating an extremely tight barrier that restricts the transport of molecules into the brain. The blood-brain barrier within the brain, the blood-spinal cord barrier within the spinal cord, and the blood-retinal barrier within the retina, are contiguous capillary barriers within the central nervous system (CNS), and are collectively referred to herein as the blood-brain barrier or BBB.

As used herein, the term "derivative" refers to derivatives of noribogaine that maintain or enhance the activity of noribogaine, or are metabolized within the patient to form noribogaine. Suitable derivatives are disclosed in U.S. patent application Ser. No. 13/104,410, entitled Substituted Noribogaine, filed on May 10, 2011, which is hereby incorporated by reference in its entirety.

As used herein, the term "pharmaceutically acceptable excipient to enhance blood brain barrier penetration" refers to a substance that is capable of disrupting or penetrating the blood brain barrier. In one embodiment, the disruption is a transient disruption. The amount of pharmaceutically acceptable excipient administered with the noribogaine or derivative thereof is the amount effective to disrupt the blood brain barrier and allow noribogaine to enter the brain.

As used herein, the term "biocompatible dehydrating saccharide" refers to a saccharide or derivative thereof, having at least 6 carbon atoms (which may be linear, branched or cyclic) with an oxygen, nitrogen or sulfur atom bonded to each carbon atom. The term "biocompatible dehydrating oligosaccharides" includes oligosaccharides containing from about 2-9 monosaccharide units. Specific monosaccharides include $C_5$ and above (preferably $C_5$-$C_8$) saccharides such as ethritol, zylitol, galactose, lactose, xylose, dulcitol, myo-inositol, fructose, mannitol, sorbitol, glucose, arabinose, arabinose, celloboise, maltose, raffinose, rhamnose, melibiose, ribose, adonitol, arabitol, arabitol, fucose, lyxose, lyxose, lyxose, glucosamine, mannosamine, and galactosamine; di- and trisaccharides include saccharides having two or three monosaccharide units.

As used herein, the term "mannitol" refers to (2R,3R,4R,5R)-hexane-1,2,3,4,5,6-hexyl

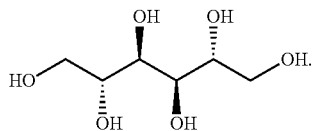

Mannitol is a polyol and has been used as an osmotic diuretic agent and a weak renal vasodilator. It was originally isolated from the secretions of the flowering ash, called manna after their resemblance to the Biblical food, and is also be referred to as mannite and manna sugar. Mannitol and derivatives thereof are readily available from commercial sources or can be synthesized using procedures known in the art. In its pyranose or condensed form, mannitol becomes a 6 membered ring saccharide (sugar) of the formula:

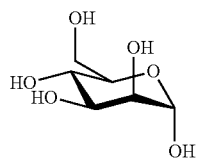

and is referred to as α-D-mannopyranose. As used herein, all saccharides are meant to include both their open forms as well as their pyranose forms including their naturally occurring D or L forms of the saccharide.

As used herein, the term "pharmaceutically acceptable salt" refers to salts derived from organic or inorganic acids. Examples of such acids include, without limitation, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like.

As used herein, the term "biocompatible, cleavable linking group" refers to a linking group that can be attached to noribogaine at any possible position such that the linker is biocompatible (i.e. does not produce undesired side effects or have an intolerable toxicity), is readily cleaved in the body (preferably in the brain), and does not inhibit or alter the desired physiological effect of noribogaine. Specifically, the linking group should be sufficiently stable in the circulatory system (serum or blood), but is cleaved to release the noribogaine upon entry into the brain. Suitable biocompatible, cleavable linking groups comprise from 1 to 20 atoms selected from carbon, nitrogen, oxygen, sulfur, and phosphorus, and are, in general, susceptible to cleavage conditions or agents in the brain (i.e. pH, redox potential or the presence of degradative molecules such as enzymes). The biocompatible, cleavable linking group can be an ester-based cleavable linking group (—C(O)O— or —OC(O)—), an amide-based cleavable linking group (—C(O)NR— or —NRC(O)—), or a phosphate-based cleavable linking group (—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(OR)—S—, —S—P(S)(OR)—O—, —O—P(O)(R)—O—, —O—P(S)(R)—O—, —S—P(O)(R)—O—, —S—P(S)(R)—O—, —S—P(O)(R)—S—, or —O—P(S)(R)—S—) where R can be hydrogen or alkyl.

As used herein, the term "alkyl" refers to a monovalent saturated aliphatic hydrocarbyl group having from 1 to 12 carbon atoms, or 1 to 6 carbon atoms. The term "Cx" means an alkyl group with x carbon atoms. In some embodiments, one or more of the hydrogen atoms of the alkyl group can be replaced with a functional group such as —OH, —NH$_2$, —SH, and the like. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). As used herein, the term "alkoxy" refers to O-alkyl.

As used herein, the term "therapeutically acceptable amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
  preventing or protecting against the disease or condition, that is, causing the clinical symptoms not to develop, for example, in a subject at risk of suffering from such a disease or condition, thereby substantially averting onset of the disease or condition;
  inhibiting the disease or condition, that is, arresting or suppressing the development of clinical symptoms; and/or
  relieving the disease or condition that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the term "patient" refers to mammals and includes humans and non-human mammals.

Excipients for Penetrating the Blood Brain Barrier

The blood brain barrier (BBB) functions to protect the brain from exposure to toxins, both endogenous and exogenous. However, this protection severely limits the therapeutic ability of many of drugs by inhibiting their crossing from the circulatory system into the brain. In order for a drug to enter the brain and cross the BBB, molecules must either passively diffuse or be actively transported across the BBB. Water soluble or polar compounds must be actively transported across the BBB, whereas it has been shown that drugs which passively diffuse into the brain have fewer hydrogen bond donors, fewer positive charges, greater lipophilicity, lower polar surfaces, reduced flexibility, and are small (i.e. less than 400-500 Da) (see Pardridge Molecular Interventions, 2003, 3:2, 90-105, Deeken, et al. Clin Cancer Res, 2007, 13:6, 1663-1674 and references cited therein). However, in some instances, a pharmaceutically acceptable excipient can be used to enhance blood brain barrier penetration (see Pan, et al. Acta Pharmacol Sin, 2000, 21:7, 613-616). This invention is relates to increased cranial delivery of noribogaine by use of a pharmaceutically acceptable excipient to enhance blood brain barrier penetration.

It is contemplated that the pharmaceutically acceptable excipient cooperatively increases the concentration of noribogaine in the brain of the treated patient thereby reducing the systemic concentration of noribogaine in the remainder of the patient's body. While not all drugs react cooperatively with blood brain barrier excipients, it is contemplated that noribogaine will show a significant increase in cranial concentration when used in conjunction with such an excipient. It is further contemplated that in view of such targeted delivery, the amount of noribogaine required to effect therapy will be reduced. In addition, it is contemplated that the compositions disclosed herein provide for an increased serum half-life when compared to noribogaine alone.

In one embodiment, the present invention is directed to a pharmaceutical composition comprising a therapeutically effective amount of noribogaine, or a derivative or pharmaceutically acceptable salt thereof, and an effective amount of a pharmaceutically acceptable excipient to enhance the blood brain barrier penetration of noribogaine. Methods for the synthesis and purification of noribogaine to be used in the compositions of the present invention are disclosed in U.S. patent application Ser. No. 13/104,406, entitled Methods and Compositions for Preparing and Purifying Noribogaine, filed on May 10, 2011, which is hereby incorporated by reference in its entirety. Suitable derivatives are disclosed in U.S. patent application Ser. No. 13/104,410, entitled Substituted Noribogaine, filed on May 10, 2011, which is hereby incorporated by reference in its entirety.

In the present invention, the composition comprises an excipient capable of transiently disrupting the BBB and allowing noribogaine to penetrate the blood brain barrier. The disrupting effects of such excipients should not produce functional neurological deficits, long-term brain edema, or brain pathology. In one embodiment, the composition comprises a hypertonic solution which transiently disrupts the BBB by causing the cells which make up the BBB to dehydrate and shrink. This dehydration and shrinkage disrupts the BBB by compromising the tight junctions between the cells and thus forming passages into the brain.

In a certain embodiment, the excipient which enhances the blood brain barrier penetration of noribogaine is a biocompatible dehydrating saccharide, such as mannitol. Suitable concentrations are known to those of skill in the art or can be readily determined using known methods. In one embodiment, it is contemplated that the concentration of mannitol in the composition is about 1.1 M. In another embodiment, mannitol is administered at a concentration of from about 0.1 mol/L to about 10 mol/L, or alternatively, at a concentration of from about 0.5 mol/L to about 5 mol/L.

Other excipients which are contemplated to be capable of enhancing penetration of noribogaine across the blood brain barrier include saccharides or saccharide derivatives (i.e. amino saccharides), bradykinin B2 receptor agonists (i.e. Cereport®), small fat-soluble molecules (i.e. ethanol or ethanol derivatives), naturally occurring or synthetic amino acids, choline, and purine bases or nucleosides or derivatives thereof. Other blood brain barrier excipients can be used that are known to those of ordinary skill in the art. Exemplary saccharides which can be used in the compositions and methods disclosed herein include, any one or more of ethritol, zylitol, galactose, lactose, xylose, dulcitol, myo-insoitol, fructose, mannitol, sorbitol, glucose, arabinose, arabinose, celloboise, maltose, raffinose, rhamnose, melibiose, ribose, adonitol, arabitol, arabitol, fucose, lyxose, lyxose, lyxose, glucosamine, mannosamine, and galactosamine. Excipients may also comprise one or more naturally occurring (endogenous or exogenous) or synthetic amino acid or derivative thereof, such as arginine, asparagine, aspartic acid, cysteine, glutamic acid, glycine, histidine, leucine, methionine, phenylalanine, proline, serine, threonine, glutamine, lysine, tryptophan, tyrosine, valine, taurine and L-dopa (a naturally occurring amino acid, dihydroxyphenyalanine, found in broad beans).

Biocompatible, Cleavable Linking Groups

In one embodiment of the present invention, at least a portion of the excipient capable of enhancing blood brain barrier penetration is bound to the noribogaine via a covalent bond or a biocompatible, cleavable linking group. The covalent bond or linking group can be attached to the noribogaine at any possible position such the bond or biocompatible linker is readily cleaved in the body and does not inhibit or alter the desired physiological effect of noribogaine. Specifically, the linking group should be sufficiently stable in the circulatory system, but is cleaved to release the noribogaine upon entry into the brain. In one embodiment, the linking group is at least 2 time and preferably at least 10 times more reactive in the brain than in the circulatory system (i.e. in the blood or serum).

Suitable biocompatible, cleavable linking groups comprise a covalent bond and a linking group having from 1 to 20 atoms selected from carbon, nitrogen, oxygen, sulfur, and phosphorus, and are, in general, susceptible to cleavage conditions or agents in the brain (i.e. pH, redox potential or the presence of degradative molecules such as enzymes, e.g., proteases, lipases, etc.). Generally, the cleavage conditions or agents should be more prevalent or found at higher levels or activities in the brain than in serum or blood. Examples of degradative agents include: redox agents which are selected for particular substrates or which have no substrate specificity, including, e.g., oxidative or reductive enzymes or reductive agents such as esterases; enzymes that can hydrolyze or degrade an acid cleavable linking group by acting as a general acid, peptidases (which can be substrate specific), and phosphatases.

Biocompatible, cleavable ester-based linking groups are cleaved by enzymes such as esterases and amidases in the brain. Ester-based cleavable linking groups comprise a cleavable ester group of the general Formula —C(O)O— or —OC(O)—. Such ester-based groups can be cleaved by esterases, for example. Biocompatible, cleavable amide-based cleavable linking groups comprise amide bonds formed between amino acids and includes the amide group —C(O)NR— or —NRC(O)— where R can be hydrogen or alkyl. Amide-based cleavable linking groups can be cleaved by enzymes such as peptidases and proteases. Biocompatible, cleavable phosphate-based cleavable linking groups are cleaved by agents that degrade or hydrolyze the phosphate group, such as phosphatases. Examples of phosphate-based linking groups can include —P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(OR)—S—, —S—P(S)(OR)—O—, —O—P(O)(R)—O—, —O—P(S)(R)—O—, —S—P(S)(R)—O—, —S—P(O)(R)—S—, —O—P(S)(R)—S— where R can be hydrogen or alkyl. Exemplary linking groups are shown in Scheme 2.

In general, the suitability of a candidate cleavable linking group can be evaluated by testing the ability of a cleaving agent (or condition) to cleave the linking group. It will also be desirable to also test the linking group for the ability to resist cleavage in the serum, blood or when in contact with other non-target tissue. Thus one can determine the relative susceptibility to cleavage between a first and a second condition, where the first is indicative of cleavage in the brain and the second is indicative of cleavage in serum, blood or other non-target tissue. Such evaluations can be carried out in cell-free systems, in cells, in cell culture, in organ or tissue culture, or in whole animals. In preferred embodiments, the cleavable linking group is cleaved at least 2, 4, 10 or 100 times faster in the brain as compared to serum, blood or other non-target tissue.

Compounds of the Invention

In one embodiment of the present invention is provided a compound of Formula I:

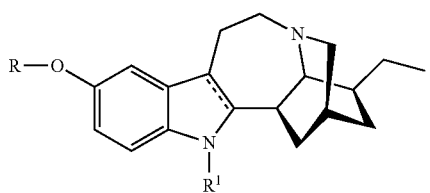

I wherein
=== is a single or double bond;
R is hydrogen, alkyl, —C(O)-alkyl, or the group -L-S where L is a covalent bond or is a biocompatible, cleavable linking group and S is a dehydrating saccharide or oligosaccharide;

$R^1$ is hydrogen or the group -L-S where L is a covalent bond or is a biocompatible, cleavable linking group and S is a dehydrating saccharide or oligosaccharide; provided that at least one of R and $R^1$ is -L-S;
or a pharmaceutically acceptable salt thereof.

In a certain embodiment, R is hydrogen and $R^1$ is -L-S. In some embodiments, R is —C(O)-alkyl and $R^1$ is -L-S. In another embodiment, R is -L-S and $R^1$ is hydrogen. In yet another embodiment, R and $R^1$ are -L-S.

In the present invention, S can be a saccharide or saccharide derivative such as an amino saccharide, provided that the saccharide is capable of disrupting or penetrating the BBB. For example, S can be a saccharide or amino saccharide from the group consisting of ethritol, zylitol, galactose, lactose, xylose, dulcitol, myo-insoitol, fructose, mannitol, sorbitol, glucose, arabinose, arabinose, celloboise, maltose, raffinose, rhamnose, melibiose, ribose, adonitol, arabitol, arabitol, fucose, lyxose, lyxose, lyxose, glucosamine, mannosamine, and galactosamine. In a preferred embodiment, S is mannitol. In another preferred embodiment, S is glucose.

In one embodiment of the compounds of the present invention, R is hydrogen, mannopyranose, glucopyranose, glucopyranose-O—$(CH_2)_9$C(O)—, ribofuranose, or ribopyranose. In another embodiment, $R^1$ is hydrogen, glucopyranose-O—$(CH_2)_8$C(O)—, —C(O)O$(CH_2CH_2O)_3$$CH_3$ or —$CO_2CH_2CH_3$. In yet another embodiment, R is hydrogen, mannopyranose, glucopyranose, glucopyranose-O—$(CH_2)_9$C(O)—, ribofuranose, or ribopyranose, and $R^1$ is hydrogen. In yet another embodiment, R is hydrogen and $R^1$ is hydrogen, glucopyranose-O—$(CH_2)_8$C(O)—, —C(O)O$(CH_2CH_2O)_3$$CH_3$ or —$CO_2CH_2CH_3$.

In one embodiment of the compounds of the present invention, === is a single bond. In another embodiment, === is a double bond.

In one embodiment of the compounds of the present invention, L is a suitable biocompatible, cleavable linking group comprising from 1 to 20 atoms selected from carbon, nitrogen, oxygen, sulfur, and phosphorus, and is, in general, susceptible to cleavage conditions or agents in the brain. In one embodiment, the linking group is an ester-based linking group. In another embodiment, the linking group is an amide-based linking group. In yet another embodiment, the linking group is a phosphate-based linking group. In another embodiment of the compounds of this invention, L is a covalent bond.

Also disclosed herein is a pharmaceutical composition comprising a pharmaceutically acceptable excipient and a therapeutically acceptable of a compound of Formula I. In a certain embodiment, R is hydrogen and $R^1$ is -L-S. In some embodiments, R is —C(O)-alkyl and $R^1$ is -L-S. In another embodiment, R is -L-S and $R^1$ is hydrogen. In yet another embodiment, R and $R^1$ are -L-S. In a preferred embodiment, S is mannitol. In another preferred embodiment, S is mannose. In yet another preferred embodiment, S is glucose.

Specific compounds of Formula I which exemplify the present invention are shown below in Table 1.

TABLE 1

| No. | Structure | R | $R^1$ |
|---|---|---|---|
| 1 | 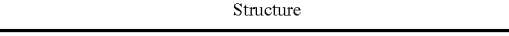 | Mannopyranose | H |

TABLE 1-continued

| No. | Structure | R | R¹ |
|---|---|---|---|
| 2 | 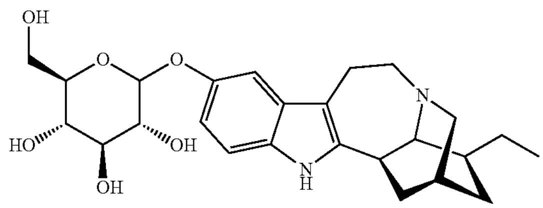 | Glucopyranose | H |
| 3 | 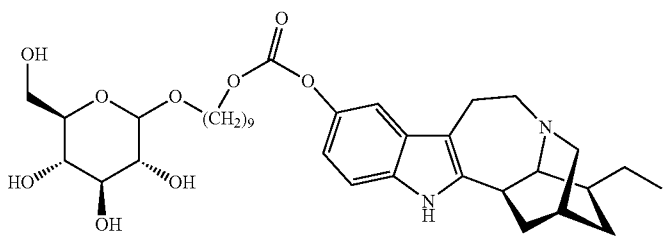 | Glucopyranose-O—(CH$_2$)$_9$C(O)— | H |
| 4 | 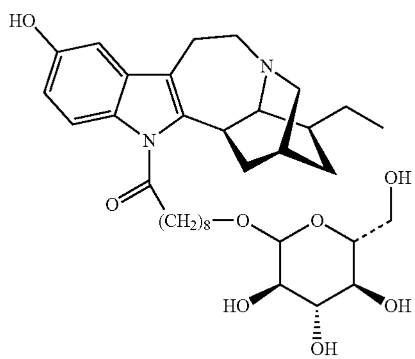 | H | Glucopyranose-O—(CH$_2$)$_8$C(O)— |
| 5 | 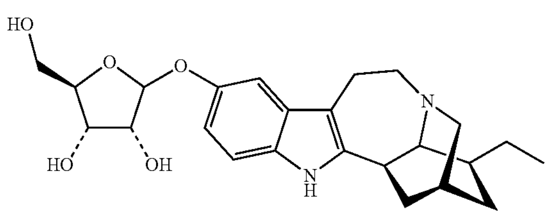 | Ribofuranose | H |
| 6 | 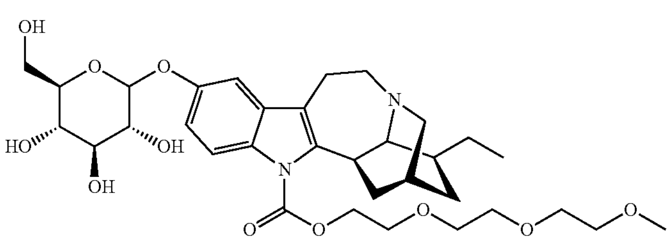 | Glucopyranose | —C(O)O—(CH$_2$CH$_2$O)$_3$—CH$_3$ |
| 7 | 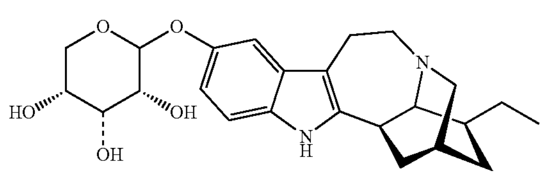 | ribopyranose | H |

TABLE 1-continued

| No. | Structure | R | R¹ |
|---|---|---|---|
| 8 | 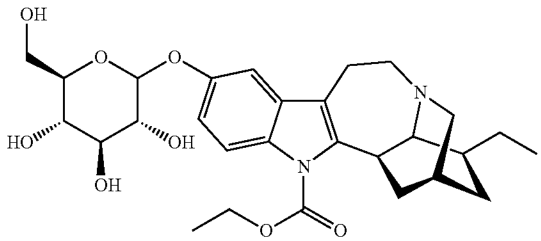 | Glucopyranose | —CO$_2$CH$_2$CH$_3$ |

Compounds of the invention can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene, P. G. M. Wuts, Protective Groups in Organic Synthesis, 4$^{th}$ Edition, Wiley-Interscience, New York, 2006, and references cited therein. The starting materials for the following reactions are generally known compounds or can be prepared by known procedures or obvious modifications thereof. For example, many of the starting materials are available from commercial suppliers such as Aldrich® Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Compounds of Formula I can be readily prepared from noribogaine by methods known to one of skill in the art. Noribogaine can be synthesized via ibogaine O-demethylation. This may be accomplished, for example, by reacting ibogaine with boron tribromide/methylene chloride at room temperature and then purifying the product using known procedures. In addition, noribogaine may also be obtained from the National Institute on Drug Abuse (Rockville, Md.). Ibogaine may be obtained from natural or commercial sources, or can be synthesized by methods known in the art (see Huffman, et al., J. Org. Chem. 50:1460 (1985)).

For example, as shown in Scheme 1, noribogaine can be reacted with a saccharide-linking group conjugate (LG-L-S, where LG is a leaving group such as alkoxy, halo, etc.) to form compounds of formula I. In certain embodiments (i.e. when R is H), the phenol is protected with a suitable protecting group (PG-LG where LG is a leaving group such as alkoxy, halo, etc.) such that the indole nitrogen is derivatized with -L-S. Suitable protecting groups are well known in the art (see T. W. Greene, P. G. M. Wuts, Protective Groups in Organic Synthesis, 4$^{th}$ Edition, Wiley-Interscience, New York, 2006). In an alternative embodiment (i.e. when R¹ is H), the indole nitrogen is protected with a suitable protecting group (PG) (see Greene et al., supra) such phenol that is derivatized with -L-S. In another alternative embodiment, both the indole nitrogen and the phenol are both derivatized with -L-S groups.

Scheme 1

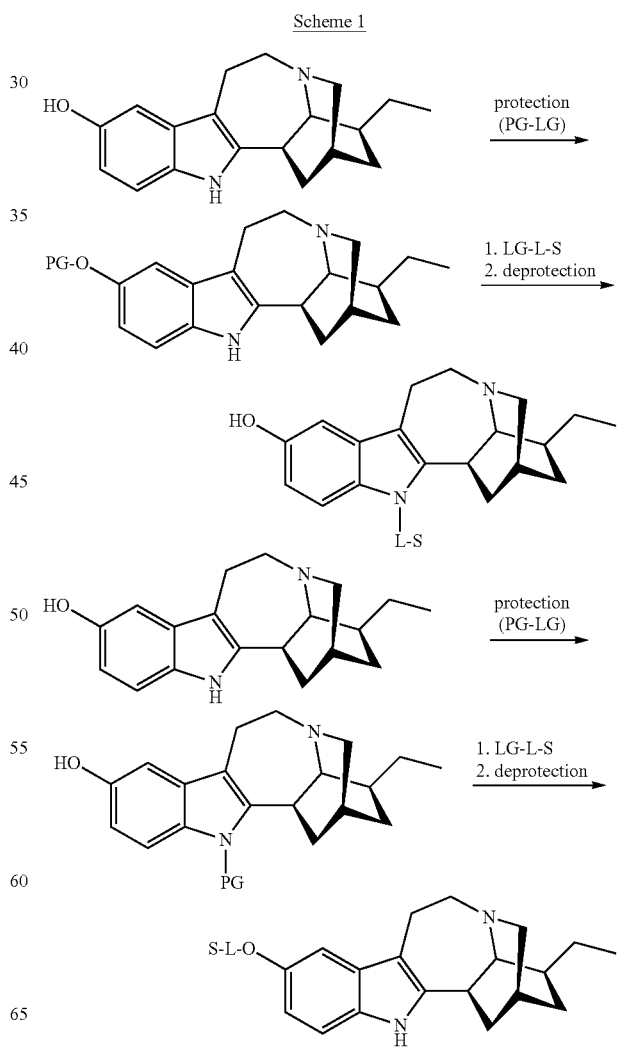

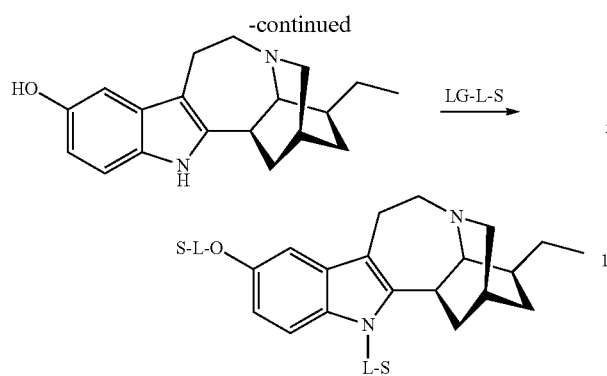

Saccharide-linking group conjugates for use in the reactions depicted in Scheme 1 (LG-L-S, where LG is a leaving group such as alkoxy, halo, etc.) can be synthesized using methods known in the art. The starting compounds are commercially available from sources such as Aldrich® Chemical Company. For example, in one embodiment, the saccharide-linking group conjugate for use in the reactions depicted in Scheme 1 is of the formula S—O—$(CH_2)_n$—CO—$OCH_3$ where S is the saccharide, n is an integer from 0 to 16 and —$OCH_3$ is the leaving group (LG) (Scheme 2, where R is H or L-S) (see U.S. Pat. No. 5,877,187). In certain embodiments, n is an integer from 5 to 10. The structures resulting from such functionalization include the following (where for illustrative purposes only α-D-mannopyranose is used as the saccharide):

sides, etc. The particular leaving group is selected relative to the functionality to which the saccharide is to be attached. For example, in Scheme 1, attachment of the saccharide to the indole nitrogen of noribogaine can be accomplished via the hydroxyl protected compound leaving only the amino group to couple with saccharide resulting in the formation of an N-linked sugar. Alternatively, coupling of the saccharide to the hydroxyl group would entail reacting the N-protected noribogaine with the appropriate functionalized sugar. Still further, using noribogaine and an excess of functionalized saccharides would provide for both the O- and N-functionalized noribogaine. The structures resulting from such functionalization include the following (where for illustrative purposes only α-D-mannopyranose is used as the saccharide):

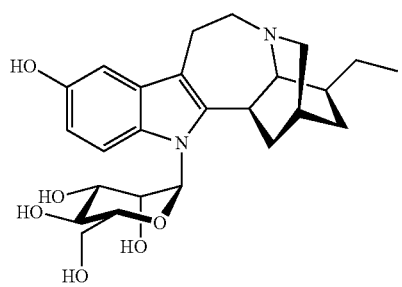

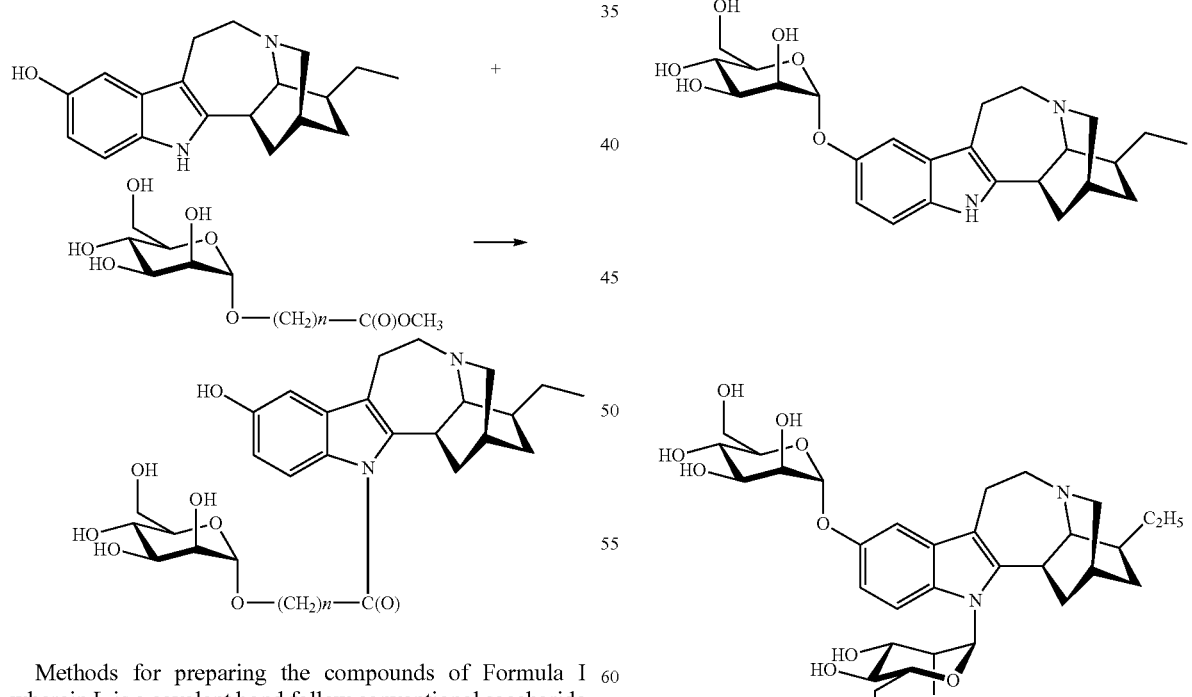

Methods for preparing the compounds of Formula I wherein L is a covalent bond follow conventional saccharide chemistry. See, for example, U.S. Pat. No. 5,877,187 which is incorporated herein by reference in its entirety. In one example, the anomeric carbon atom at the 1-position of a saccharide is chemically modified by conventional techniques to introduce a leaving group. Suitable leaving groups comprise halides, trichloroacetimidates, acetyl, thioglyco- Exemplary compounds of this invention wherein L is a linking group can be prepared by the synthetic protocols illustrated below in Scheme 3.

Scheme 3

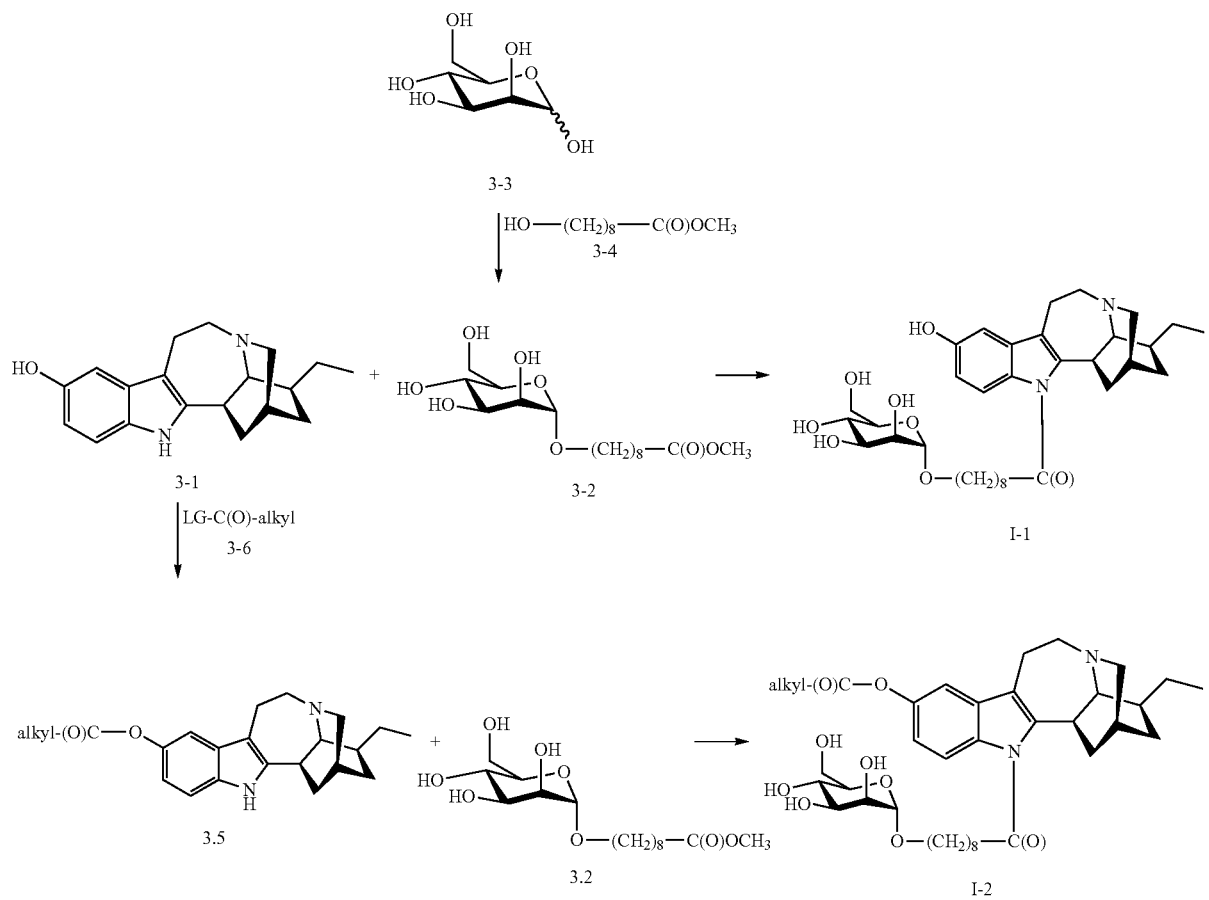

Noribogaine (3-1) can be modified with a saccharide-linking group conjugate (3-2), or a protected derivative thereof (e.g., the polyacetate or polybenzylate), to form a compound of formula I-1 under conventional amidation conditions well known in the art. Optionally, the indole nitrogen of 3-1 or the hydroxyl groups of 3-2 can be protected using suitable protecting groups prior to the reaction of 3-1 with 3-2 and then subsequently deprotected using conditions known in the art. Compound 3-2 can be prepared from reacting at least a stoichiometric amount and preferably an excess of compound 3-4 with a suitable saccharide (3-3). The reaction can be conducted under conventional coupling conditions well known in the art as the anomeric carbon atom of the saccharide will preferably react with the hydroxyl group of the linker 3-2. In one embodiment, the reaction is conducted in a polar solvent. Upon reaction completion, the compounds I-1 can be recovered by conventional techniques such as neutralization, extraction, precipitation, chromatography, filtration and the like; or, alternatively, used without purification and/or isolation.

Compounds 3-5 for use in the reactions depicted in Scheme 3, can be prepared by reacting compounds 3-6 (LG is preferably, but not limited to alkoxy or halo) with 3-1 under conventional esterification conditions. Optionally, the indole nitrogen of 3-1 can be protected using a suitable protecting group prior to the reaction of 3-1 with 3-6 and then subsequently deprotected using conditions known in the art. Compound 3-5 can then be modified with 3-2 to form a compound of formula I-2 under conventional amidation conditions well known in the art. Upon reaction completion, I-2 can be recovered by conventional techniques such as neutralization, extraction, precipitation, chromatography, filtration, and the like; or, alternatively, used without purification and/or isolation.

Methods for preparing the compounds of Formula I-3 or I-4 wherein L is a covalent bond follow conventional saccharide chemistry. As Shown below in Scheme 4, compounds of formula 4-1 can be prepared by the chemical modification of the anomeric carbon of 3-3 (e.g. mannose) by conventional techniques to introduce a leaving group LG (e.g. a halide, trichloroacetimidate, acetyl group, a thioglycoside, and the like). The particular leaving group is selected relative to the functionality to which 4-1 is to be attached. The coupling of 4-1 to the indole nitrogen of 3-1 or 3-5 can be accomplished using typical coupling conditions known to one of skill in the art resulting in the formation of an N-linked sugar. Further, the hydroxyl groups of 3-3 or 4-1 can be protected using a suitable protecting group and then subsequently deprotected using conditions known in the art. Upon reaction completion, I-3 or I-4 can be recovered by conventional techniques such as neutralization, extraction, precipitation, chromatography, filtration, and the like; or, alternatively, used without purification and/or isolation.

Scheme 4

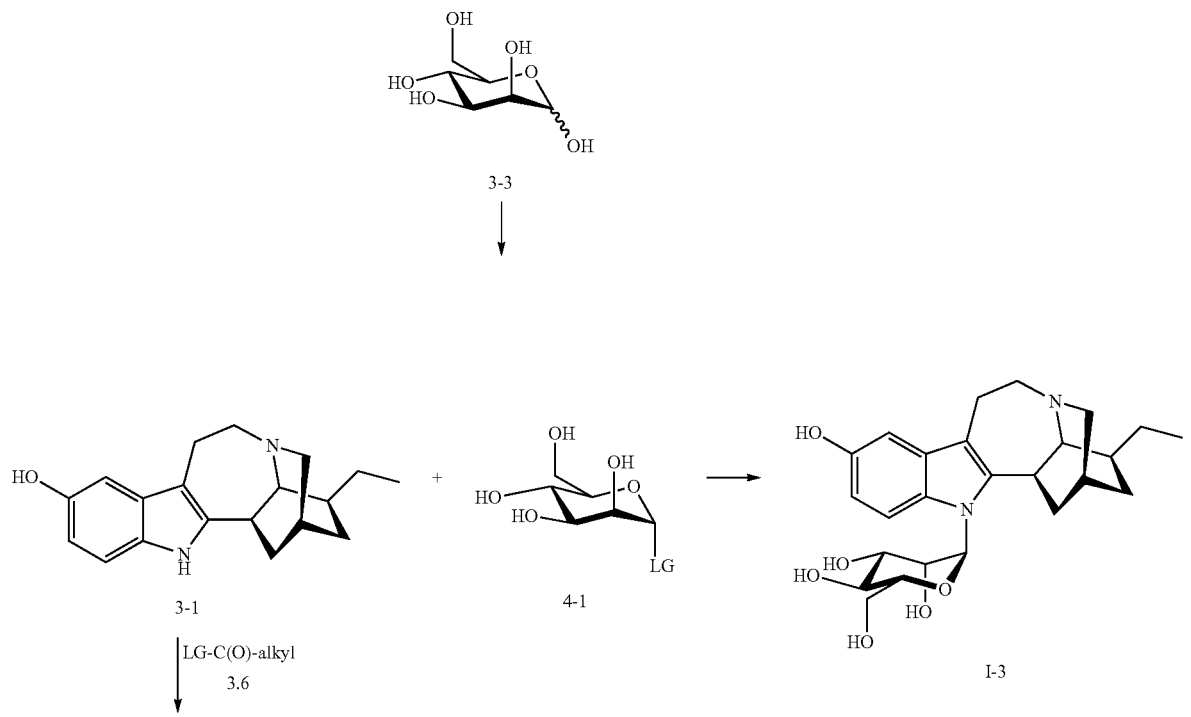

Alternatively, as shown in Scheme 5, coupling of the saccharide to the phenol moiety of 3-1 can proceed via reacting 3-1 with the appropriately functionalized 4-1. Although not shown, it is contemplated that 3-1 may couple with the anomeric carbon atom of 3-3 under certain reaction conditions without the need for a leaving group. Optionally, the indole nitrogen of 3-1 or the hydroxyl groups of 4-1 or 3-3 can be protected using suitable protecting groups (e.g., the hydroxyl groups of 4-1 can be protected as the polyacetate or polybenzylate), and then subsequently deprotected using conditions known in the art.

Scheme 5

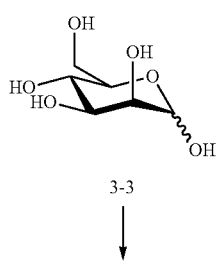

-continued

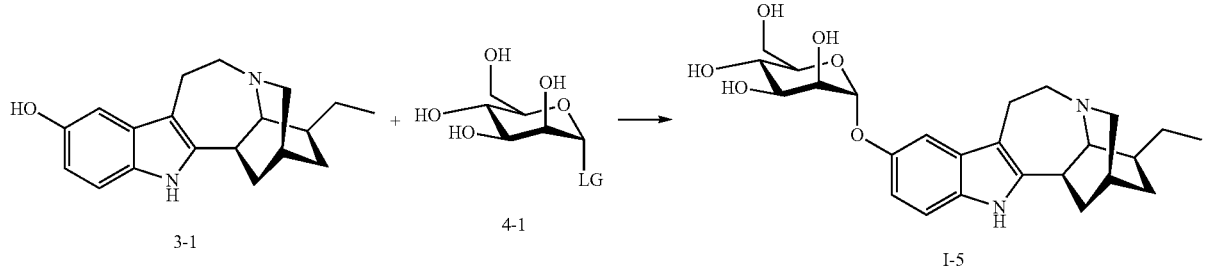

Chemical reactions as described above are known in the art and are exemplified in U.S. Pat. Nos. 5,877,157 and 6,174,867, which are incorporated herein by reference in their entirety.

METHODS OF THE INVENTION

Noribogaine, a metabolite of ibogaine, has properties that are well suited to the treatment of pain and to the withdrawal symptoms associated with drug dependency or abuse. In particular, it has been discovered that noribogaine binds to two classes of opioid receptors that have been associated with pain relief, the $\mu$ and $\kappa$ receptors. In the case of the $\mu$-type receptors, it appears that noribogaine acts as a full opiate agonist. In addition, noribogaine elevates brain serotonin levels by blocking synaptic reuptake. It is believed that such levels (as well as ligand interactions at the $\mu$ and $\kappa$ opiate receptors) play a role in the anxiety and drug cravings experienced by addicts during withdrawal.

Treatment of Pain

One aspect of the present invention is directed to a method for treating pain in a patient. The pain can be any type of pain including, but not limited to neuropathic or nociceptive pain, and various types thereof including somatic, visceral and phantom pain. Accordingly, in one embodiment, the method comprises administering to said patient a pharmaceutical composition comprising a therapeutically effective amount of noribogaine, or a derivative or pharmaceutically acceptable salt thereof, and an effective amount of a pharmaceutically acceptable excipient to enhance the blood brain barrier penetration of noribogaine.

In another embodiment, the present invention is directed to a method for treating pain in a patient which method comprises administering to said patient a therapeutically effective amount of a compound of Formula I or a pharmaceutical composition comprising a therapeutically effective amount of a compound of Formula I and a pharmaceutically acceptable excipient.

Treatment of Addiction

Noribogaine has been known to be used to treat patients for alleviating the symptoms associated with withdrawal from drug dependency. Accordingly, the present invention is also directed to a method for treating addiction in a patient which method comprises administering to said patient a pharmaceutical composition comprising a therapeutically effective amount of noribogaine, or a derivative or pharmaceutically acceptable salt thereof, and an effective amount of a pharmaceutically acceptable excipient to enhance the blood brain barrier penetration of noribogaine. In another embodiment, the invention is directed to a method for treating addiction in a patient which method comprises administering to said patient a therapeutically effective amount of a compound of Formula I or a pharmaceutical composition comprising a therapeutically effective amount of a compound of Formula I and a pharmaceutically acceptable excipient.

In certain embodiments, the treatment of addiction in a patient comprises alleviating the symptoms associated with withdrawal from drug dependency. Such symptoms include nausea, vomiting, anxiety, abdominal cramps, muscle pain, chills and headache. In addition, noribogaine treatment decreases the drug cravings normally experienced by addicts after cessation of the self administration of the abused substance. It is contemplated that the compositions disclosed herein are especially useful in the treatment of addiction to narcotics such as heroin and methadone. However, it is also useful in treating patients addicted to cocaine, alcohol, amphetamines and combinations of these drugs.

Dosage and Routes of Administration

It is contemplated that any route of administration and dosage form may be compatible with the pharmaceutical compositions and methods discussed above. As the compositions disclosed herein are designed to target the brain and penetrate the blood brain barrier, it is contemplated that the dosage of noribogaine administered to the patent can be decreased in comparison to the dose administered to a patient when using noribogaine alone. That said, the appropriate dosing regimen and route of administration can be readily determined by the attending clinician.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous and subcutaneous routes. In addition, it is contemplated that the composition can be administered transdermally in which drug is applied as part of a cream, gel, or patch (for examples of transdermal Formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

It is contemplated that the dosage required for treating pain may differ from the dosage required for treating addiction, however, the dosing regimen can be readily determined by the attending clinician based on the desired treatment. It is contemplated that for the treatment of pain, the dosage of noribogaine administered to a patient may be from about 0.1 to about 100 mg per kg of body weight and, preferably, from about 0.1 to about 30 mg per kg of body weight. For the treatment of addiction, the dosage of noribogaine administered to a patient may be from about 0.1 to about 20 mg/ml.

Kit of Parts

One aspect of the present invention is directed to a kit of parts comprising a composition as disclosed herein and a means for administering the composition to a patient in need thereof. The means for administration to a patient can include, for example, any one or combination of a syringe, a needle, an IV bag comprising the composition, a vial comprising the composition, etc. In one embodiment, the kit comprises a first and a second vial, wherein the first vial comprises the pharmaceutically acceptable excipient to enhance the blood brain barrier penetration of noribogaine and the second composition comprises a therapeutically effective amount of noribogaine, or a derivative or pharmaceutically acceptable salt thereof. In such an embodiment, the pharmaceutically acceptable excipient may be administered to the patient just prior to the noribogaine composition. In one embodiment, the pharmaceutically acceptable excipient is administered to the patient about 5 to 10 minutes prior to the noribogaine composition.

EXAMPLES

The present invention is further defined by reference to the following examples. It will be apparent to those skilled in the art that many modifications, both to materials and methods, may be practiced without departing from the scope of the current invention.

TABLE 2

List of abbreviations and acronyms.

| Abbreviation | Meaning |
|---|---|
| ° C. | Degree Celsius |
| Å | Angstrom |
| Ac | Acetyl |
| aq. | Aqueous |
| atm | Atmosphere |
| Bn | Benzyl |
| bs | Broad singlet |
| Bu | Butyl |
| d | Doublet |
| DCM | dichloromethane |
| dd | Doublet of doublets |
| DMAP | 4-Dimethylaminopyridine |
| DMF | Dimethylformamide |
| Et | Ethyl |
| g | Gram |
| h | Hour |
| HPLC | High-performance liquid chromatography |
| Hz | Hertz |
| i-Pr | Isopropyl |
| IV | Intravenous |
| Kg | Kilogram |
| M | Molar |
| m | Multiplet |
| M+ | Mass peak |
| Me | Methyl |

TABLE 2-continued

List of abbreviations and acronyms.

| Abbreviation | Meaning |
|---|---|
| mg | Milligram |
| min | Minute |
| mL | Milliliter |
| mM | Millimolar |
| mmol | Millimole |
| MS | Mass spectrometry |
| N | Normal |
| NaHDMS | Sodium hexamethyldisilazane |
| NMR | Nuclear magnetic resonance |
| PEG | Polyethylene glycol |
| prep | Preparative |
| r.t./rt | Room temperature |
| s | Singlet |
| t | Triplet |
| TBS | tert-Butyldimethylsilyl |
| TBSCl | tert-Butyldimethylsilyl chloride |
| t-Bu | tert-Butyl |
| THF | Tetrahydrofuran |
| TLC | Thin layer chromatography |
| v/v | Volume/volume |
| δ | Chemical shift |
| μL | Microliter |

Example 1

Preparation of Compound 1

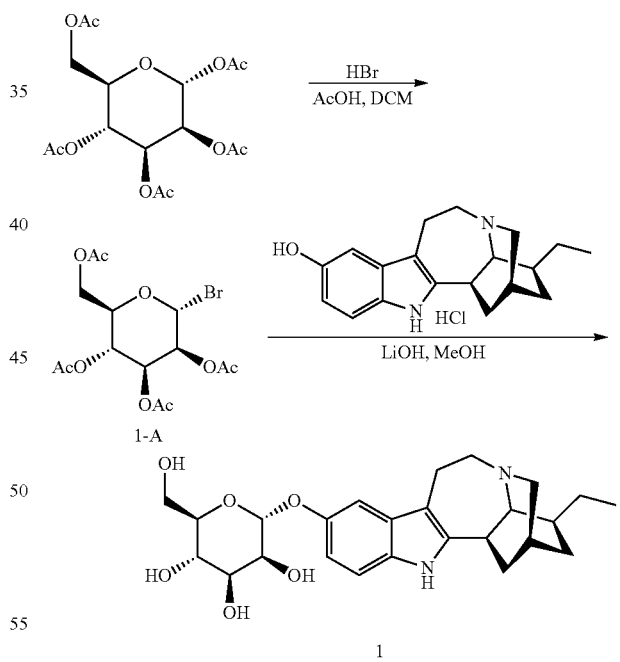

Preparation of bromide 1-A

To a solution of 1,2,3,4,6-penta-O-acetyl-D-mannopyranose (1 g, 2.56 mmol) in DCM (2 mL) was added HBr (33% in AcOH, 2.5 mL) dropwise at room temperature. The reaction mixture was stirred at room temperature for 2 h. The mixture was diluted with DCM, and washed with H$_2$O and NaHCO$_3$ (3×). The organic layer was dried and concentrated.

The crude 1-A (1.06 g, 100%) was pure enough to be used directly in the next step without further purification.

Preparation of 1

To a solution of noribogaine HCl salt (30 mg, 0.09 mmol) and bromide 1-A (74 mg, 0.18 mmol) in MeOH (2 mL) was added portionwise LiOH.H$_2$O (15 mg, 0.36 mmol). The reaction mixture was stirred at room temperature for 2 h. The solution was acidified to neutral with aq. HCl (0.5 N). The mixture was purified by prep-HPLC to give compound 1 (10 mg) as a white solid.

MS calculated for ($C_{25}H_{34}N_2O_6$): 458.2; MS found (M+1): 459.3. $^1$H NMR (CD$_3$OD) δ 8.52 (bs, 1H), 7.25 (d, 1H), 7.17 (d, 1H), 6.88 (dd, 1H), 5.38 (d, 1H), 4.02 (d, 1H), 3.93 (dd, 1H), 3.80-3.62 (m, 5H), 3.60 (m, 3H), 3.41 (m, 3H), 3.22 (m, 1H), 2.36 (t, 1H), 2.19 (m, 2H), 2.00 (m, 1H), 1.76 (dd, 1H), 1.62 (m, 2H), 1.40 (m, 1H), 1.02 (t, 3H).

Example 2

Preparation of Compound 2

Preparation of 2-A

To a solution of penta-acetyl-alpha-D-glucose (3.9 g, 10 mmol) and 1,9-nonanediol (2.4 g, 15 mmol) in DCM (35 mL) was added dropwise SnCl$_4$ (15 mmol, 1M in DCM, 15 mL). The resulting mixture was stirred at 50° C. for 4 h. The reaction mixture was diluted with DCM and H$_2$O. The organic layer was separated, washed with NaHCO$_3$, and dried and concentrated. The crude product mixture was purified by flash column chromatography (EtOAc:Hexanes/1:1) to afford compound 2-A (1.6 g, 33%).

MS calculated for ($C_{23}H_{38}O_{11}$): 490; MS found (M+1): 491

Preparation of 2-B

To a solution of 2-A (200 mg, 0.40 mmol) and N,N'-disuccinimidyl carbonate (122 mg, 0.48 mmol) in chloroform (2 mL) was added pyridine (0.042 mL, 0.52 mmol) in one portion. The mixture was stirred at rt for 3 h. Aqueous HCl (0.5 N) was used to quench the reaction. The reaction was diluted with DCM and H$_2$O. The organic layer was extracted,

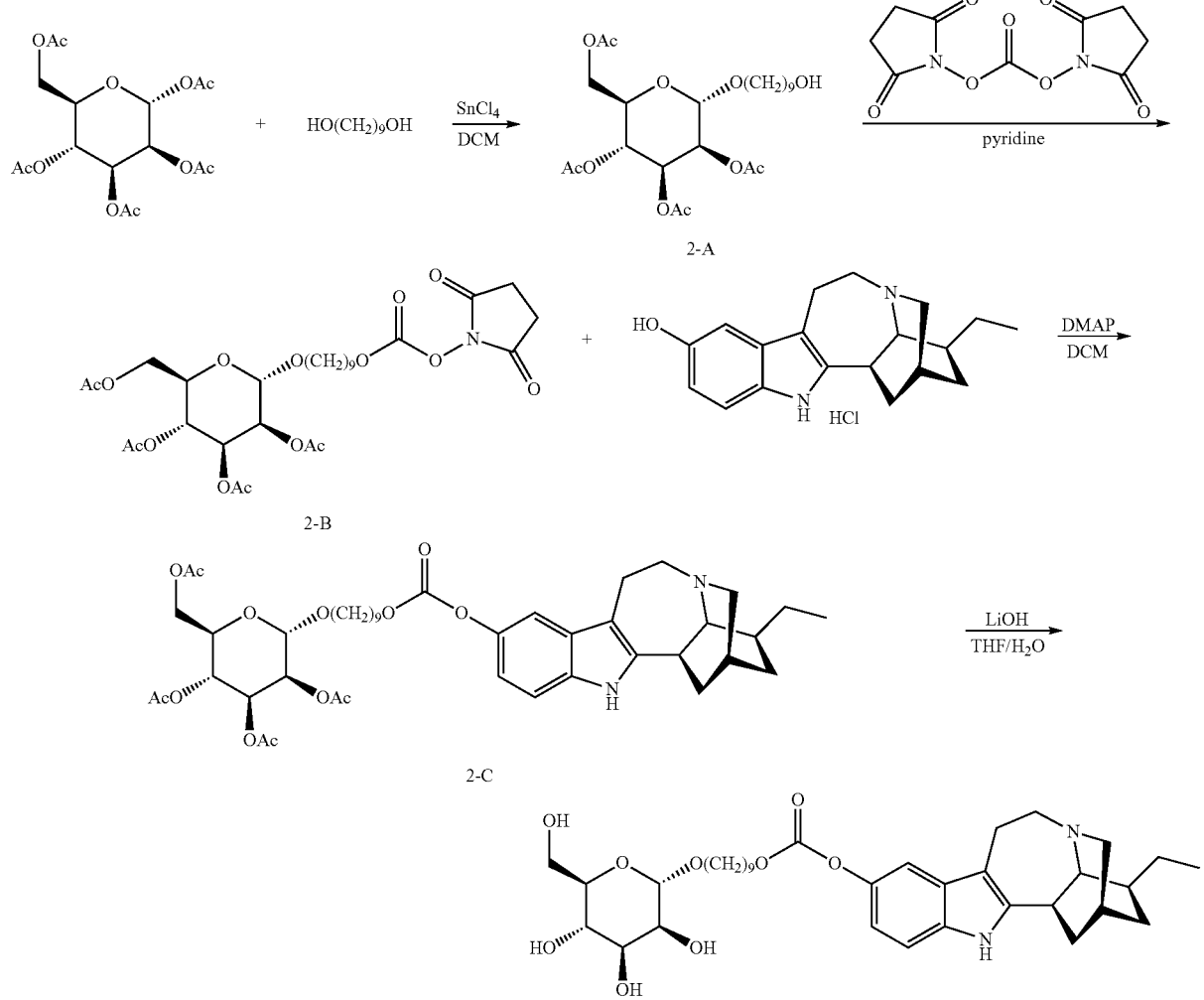

dried and concentrated to give crude compound 2-B in quantitative yield, which used in the next step without purification.

MS calculated for ($C_{28}H_{41}NO_{15}$): 631; MS found (M+1): 632

Preparation of 2-C

To a solution of 2-B (crude, 0.4 mmol) and noribogaine HCl salt (35 mg, 0.08 mmol) in DCM (2 mL) was added DMAP (112 mg, 0.92 mmol) and DIPEA (60 μL, 0.36 mmol). The reaction mixture was stirred at 40° C. for 1 h. The reaction solution was diluted with DCM and $H_2O$. The organic layer was separated, dried and concentrated, and the crude product purified by prep-TLC (DCM:MeOH, 8:1) to give product 2-C (60 mg, 92%).

MS calculated for ($C_{43}H_{60}N_2O_{13}$): 812; MS found (M+1): 813

Preparation of 2

To a solution of compound 2-C (20 mg, 0.024 mmol) in THF/$H_2O$ (2 mL:1 mL) was added LiOH (6 mg, 0.143 mmol). The reaction mixture was stirred at rt for 2 h. The reaction mixture was then acidified to neutral with 1 N aq. HCl. The crude mixture was purified by HPLC to give compound 2 (9 mg).

MS calculated for ($C_{35}H_{52}N_2O_9$): 644.4; MS found (M+1): 645.6. $^1$H NMR ($CD_3OD$) δ 8.52 (bs, 1H), 7.25 (m, 2H), 6.87 (dd, 1H), 4.76 (d, 1H), 4.22 (t, 2H), 3.80-3.50 (m, 8H), 3.42-3.35 (m, 5H), 3.25-3.08 (m, 2H), 2.32 (t, 1H), 2.14 (m, 2H), 2.03 (m, 1H), 1.77-1.58 (m, 7H), 1.48-1.32 (m, 11H), 1.02 (t, 3H).

Example 3

Preparation of Compound 3

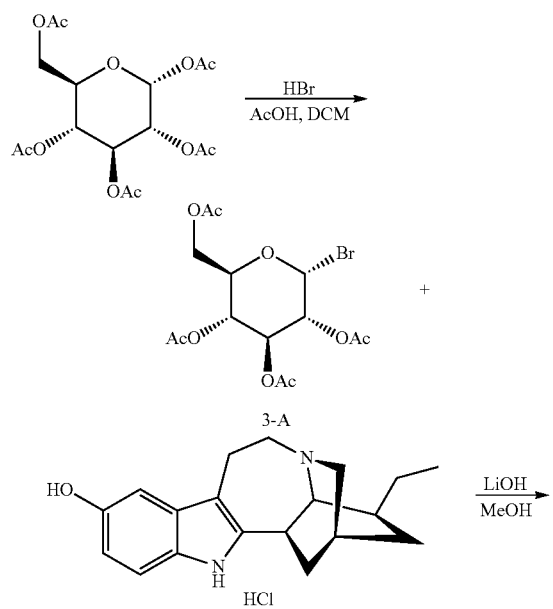

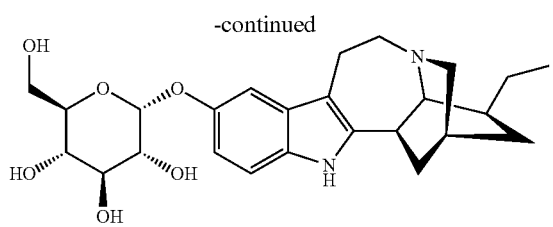

Preparation of 3-A

To a solution of penta-acetyl-alpha-D-glucose (1.0 g, 2.56 mmol) in DCM (2 mL) was added HBr (33% in AcOH, 2.5 mL) dropwise at room temperature. The reaction mixture was stirred at room temperature for 2 h. The mixture was then diluted with DCM, and washed with $H_2O$ and $NaHCO_3$ (3×). The organic layer was dried and concentrated to giver crude bromide 3-A (1.06 g, 100%), which was used directly in the next step without purification.

Preparation of 3

To a solution of noribogaine HCl salt (30 mg, 0.09 mmol) and bromide 3-A (74 mg, 0.18 mmol) in MeOH (2 mL) was added portionwise LiOH.$H_2O$ (15 mg, 0.36 mmol). The reaction mixture was stirred at room temperature for 2 h, then the solution was acidified to neutral with 0.5 N aq. HCl. The mixture was purified by prep HPLC to give compound 3 (11 mg) as a white solid.

MS calculated for ($C_{25}H_{34}N_2O_6$): 458.2; MS found (M+1): 459.3. $^1$H NMR ($CD_3OD$) δ 8.47 (bs, 1H), 7.24 (d, 1H), 7.17 (d, 1H), 6.94 (dd, 1H), 4.84 (d, 1H), 3.94 (d, 1H), 3.70 (dd, 1H), 3.62-3.54 (m, 3H), 3.42-3.38 (m, 4H), 3.36 (m, 3H), 3.20 (m, 2H), 2.30 (t, 1H), 2.13 (m, 2H), 1.99 (m, 1H), 1.77-1.58 (m, 3H), 1.39 (m, 1H), 1.03 (t, 3H).

Example 4

Preparation of Compound 4

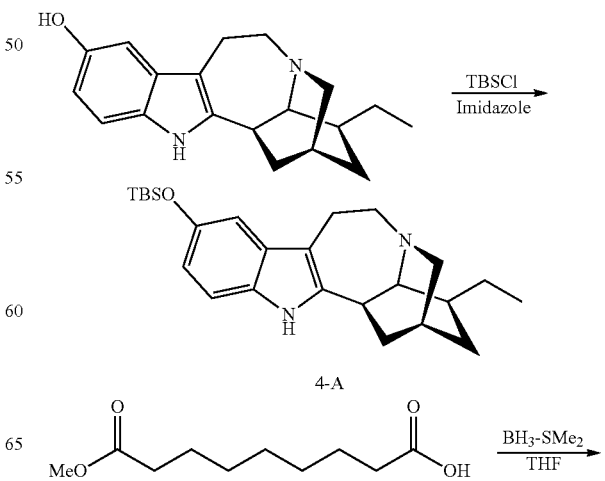

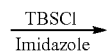

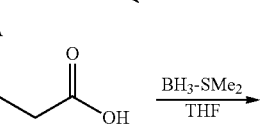

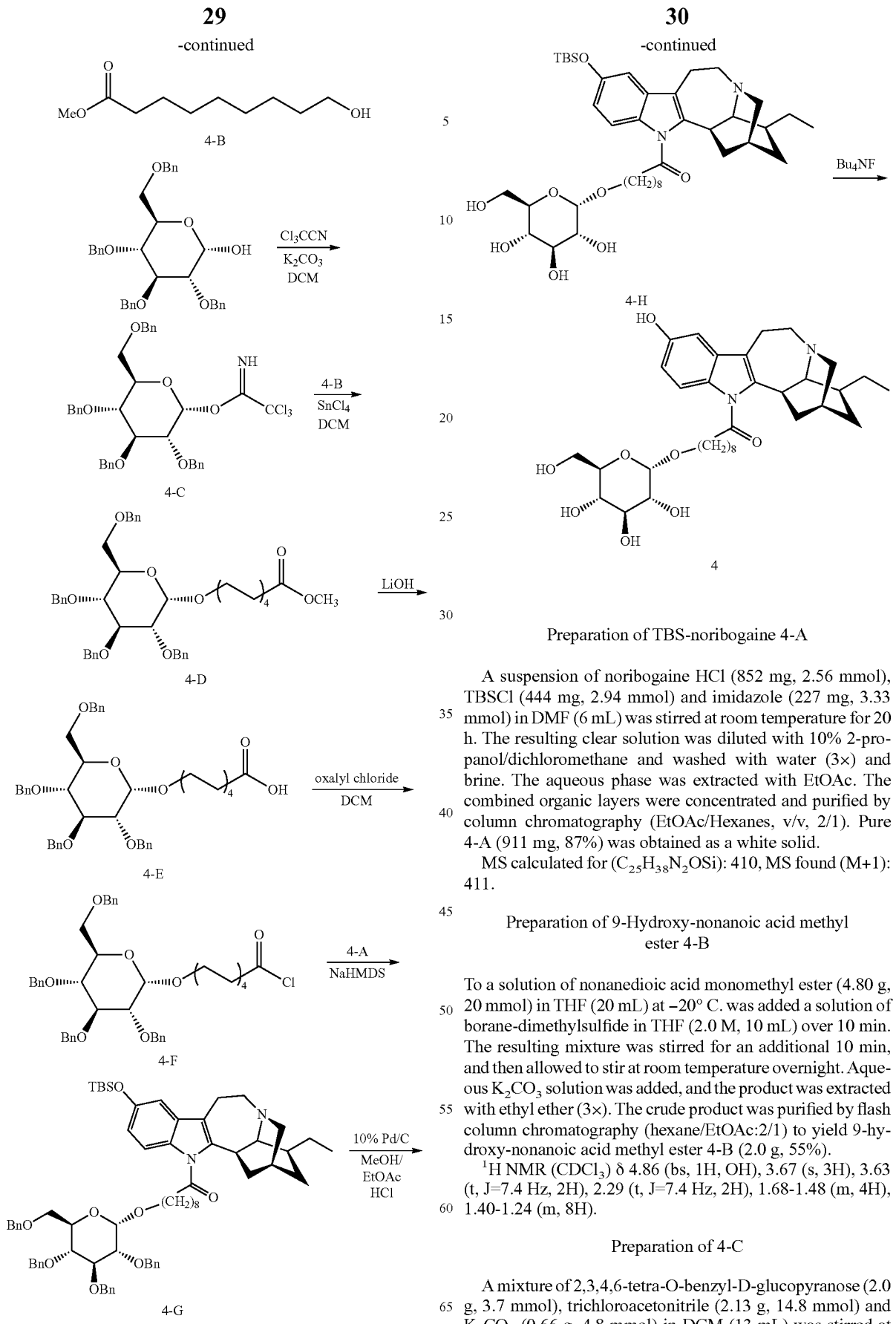

Preparation of TBS-noribogaine 4-A

A suspension of noribogaine HCl (852 mg, 2.56 mmol), TBSCl (444 mg, 2.94 mmol) and imidazole (227 mg, 3.33 mmol) in DMF (6 mL) was stirred at room temperature for 20 h. The resulting clear solution was diluted with 10% 2-propanol/dichloromethane and washed with water (3×) and brine. The aqueous phase was extracted with EtOAc. The combined organic layers were concentrated and purified by column chromatography (EtOAc/Hexanes, v/v, 2/1). Pure 4-A (911 mg, 87%) was obtained as a white solid.

MS calculated for ($C_{25}H_{38}N_2OSi$): 410, MS found (M+1): 411.

Preparation of 9-Hydroxy-nonanoic acid methyl ester 4-B

To a solution of nonanedioic acid monomethyl ester (4.80 g, 20 mmol) in THF (20 mL) at −20° C. was added a solution of borane-dimethylsulfide in THF (2.0 M, 10 mL) over 10 min. The resulting mixture was stirred for an additional 10 min, and then allowed to stir at room temperature overnight. Aqueous $K_2CO_3$ solution was added, and the product was extracted with ethyl ether (3×). The crude product was purified by flash column chromatography (hexane/EtOAc:2/1) to yield 9-hydroxy-nonanoic acid methyl ester 4-B (2.0 g, 55%).

$^1$H NMR (CDCl$_3$) δ 4.86 (bs, 1H, OH), 3.67 (s, 3H), 3.63 (t, J=7.4 Hz, 2H), 2.29 (t, J=7.4 Hz, 2H), 1.68-1.48 (m, 4H), 1.40-1.24 (m, 8H).

Preparation of 4-C

A mixture of 2,3,4,6-tetra-O-benzyl-D-glucopyranose (2.0 g, 3.7 mmol), trichloroacetonitrile (2.13 g, 14.8 mmol) and $K_2CO_3$ (0.66 g, 4.8 mmol) in DCM (13 mL) was stirred at room temperature for 3 days. The solid was removed by filtration and the filtrate was concentrated to provide a crude product 4-C (3.0 g, >100%) which was used without purification.

MS calculated for ($C_{36}H_{36}Cl_3NO_6$): 683.2; MS found (M+Na): 708

Preparation of 4-D

A solution of $SnCl_4$ in DCM (1.0 M, 1.2 mL) was slowly added into a solution of 4-B (230 mg, 1.22 mmol) and 4-C (1.25 g, 1.83 mmol) in DCM (3.5 mL) at 0° C. The resulting mixture was stirred at the temperature for 20 min, and then water was added to quench the reaction. The product was extracted with DCM, and the crude product was purified by flash column chromatography (EtOAc/hexane:1/4) to afford 4-D (400 mg, 46%).

MS calculated for ($C_{44}H_{54}O_8$): 710; MS found (M+Na): 733

Preparation of 4-E

A mixture of 4-D (400 mg, 0.56 mmol), LiOH (118 mg, 2.81 mmol) in MeOH/water/THF (2 mL/2 mL/4 mL) was stirred at room temperature for 16 h. The solution was acidified with 1 N aq. HCl to pH~3.0. The product was extracted with ethyl acetate, and the combined organic layers were dried over $MgSO_4$. After filtration and concentration, the crude product 4-E (0.39 g, quantitative) was used for next reaction without purification.

$^1$H NMR ($CDCl_3$) δ 7.40-7.12 (m, 17H), 7.08-7.05 (m, 3H), 5.02-4.38 (m, 8H), 4.00-3.92 (m, 1H), 3.78-3.38 (m, 8H), 2.34 (t, J=7.4 Hz, 2H), 1.68-1.55 (m, 4H), 1.40-1.24 (m, 8H).

Preparation of 4-F

Oxalyl chloride (59 μL, 0.68 mmol) was slowly added into a solution of acid 4-E (0.39 g, 0.57 mmol) in DCM (5 mL) at room temperature, followed by adding DMF (7 μL). The resulting mixture was stirred at the temperature for 3 h, and then concentrated. The crude product 4-F was further dried under high vacuum and used in next reaction without purification.

Preparation of 4-G

A solution of acyl chloride 4-F (104 mg, 0.25 mmol) in THF (2 mL) was cooled at −78° C., and then 0.38 mL of 1 N NaHMDS in THF was added. After 15 min a solution of 4-A (274 mg, 0.38 mmol) in THF (3 mL) was added. The reaction mixture was stirred at −78° C. for 20 min, and then allowed to slowly warmed up to room temperature. The reaction was quenched with saturated $NH_4Cl$ solution after 2 h. The product was extracted with DCM. After combination and concentration of the extracts, the crude product was purified by prep-TLC to afford 4-G (110 mg).

MS calculated for ($C_{68}H_{88}N_2O_8Si$): 1089; MS found (M+H): 1090

Preparation of 4-H

Hydrogenation of 4-G (110 mg, 0.10 mmol) was carried in EtOAc/MeOH (2 mL/3 mL) with 10% Pd/C (80 mg) as catalyst under 1 atm of hydrogen, using HCl (4 N in dioxane, 100 μL) to acidify the solution. After 48 h the mixture was filtered through a pad of Celite, and the organic layer concentrated. The crude product was purified by prep-TLC to give 4-H (17 mg, 27%).

MS calculated for ($C_{40}H_{64}N_2O_8Si$): 728; MS found (M+H): 729

Preparation of 4

TBS-protected 4-H (17 mg, 0.023 mmol) was further deprotected with $Bu_4NF$ (40 mg, 1.08 mmol) in MeOH (3 mL) at 50° C. The reaction was complete after 3 h. The crude product was purified by prep-TLC to afford the pure compound 4 (12 mg).

MS calculated for ($C_{34}H_{50}N_2O_8$): 614; MS found (M+H): 615. $^1$H NMR ($CD_3OD$) δ 7.56 (d, J=8.7 Hz, 1H), 6.88 (d, J=2.4 Hz, 1H), 6.79 (dd, J=8.7 Hz, and 2.4 Hz, 1H), 4.78 (d, J=2.1 Hz, 0.5H), 4.26 (d, J=7.8 Hz, 0.5H), 3.94-3.12 (m, 14H), 3.10-2.96 (m, 2H), 2.26-2.10 (m, 2H), 2.08-1.72 (m, 4H), 1.70-1.54 (m, 5H), 1.50-1.34 (m, 11H), 1.00 (t, J=7.2 Hz, 3H).

Example 5

Preparation of Compound 5

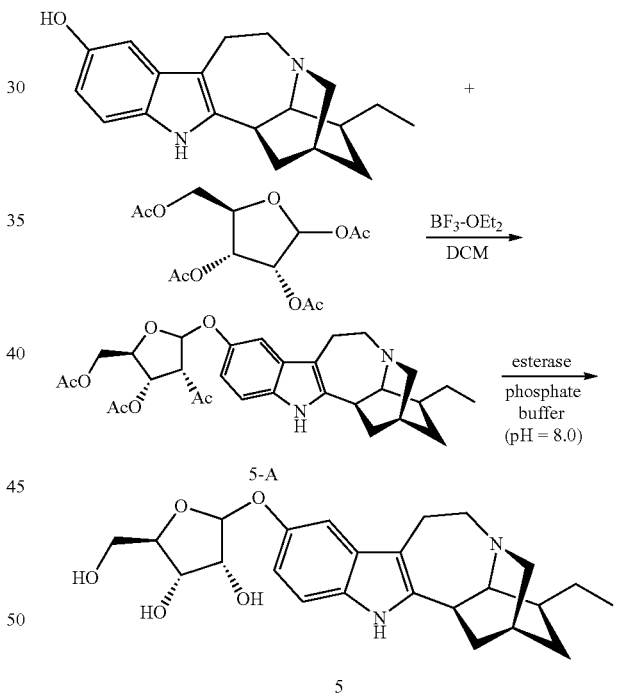

Preparation of 5-A

A mixture of noribogaine (17 mg, 0.06 mol), tetra-O-acetyl-β-D-ribofuranose (38 mg, 0.12 mmol) and 4 Å molecular sieves (1 g) in DCM (2 mL) was stirred at room temperature for 10 min. Boron trifluoride etherate complex (200 μL, 1.6 mmol) was added, and resulting mixture was stirred at the temperature for 2 h. The reaction mixture was diluted with DCM and then filtered to remove the solid. The filtrate was concentrated and further dried in high vacuum. The crude product was purified by flash column chromatography ($Et_3N$/1-PrOH/DCM: 1/10/200) to yield 7 mg of 5-A.

MS calculated for ($C_{30}H_{38}N_2O_8$): 554; MS found (M+H): 555

Preparation of 5

Esterase (from porcine liver) suspension (1 drop) was added into a solution of the triacetate 5-A (7 mg, 0.013 mmol) in 10 mL of phosphate buffer (10 mM, pH 8.0). The reaction mixture was stirred at 25° C. for 7 h, and then treated with 10 mL of MeOH. The resulting solution was concentrated to 3 mL and purified by prep-HPLC to yield 2.5 mg of the pure compound 5.

MS calculated for ($C_{24}H_{32}N_2O_5$): 428; MS found (M+H): 429. $^1$H NMR (CD$_3$OD) δ 7.16 (d, J=8.7 Hz, 1H), 7.12 (d, J=2.4 Hz, 1H), 6.81 (dd, J=8.7 and 2.4 Hz, 1H), 5.49 (d, J=1.2 Hz, 1H), 4.25-4.17 (m, 2H), 4.12-4.04 (m, 1H), 3.82-3.76 (m, 1H), 3.70-3.48 (m, 4H), 3.40-3.08 (m, 3H), 2.38-2.24 (m, 1H), 2.18-1.92 (m, 4H), 1.78-1.58 (m, 3H), 1.40-1.26 (m, 3H), 1.03 (t, J=7.2 Hz, 3H).

Example 6

Preparation of Compound 6

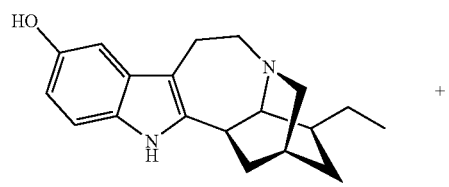

+

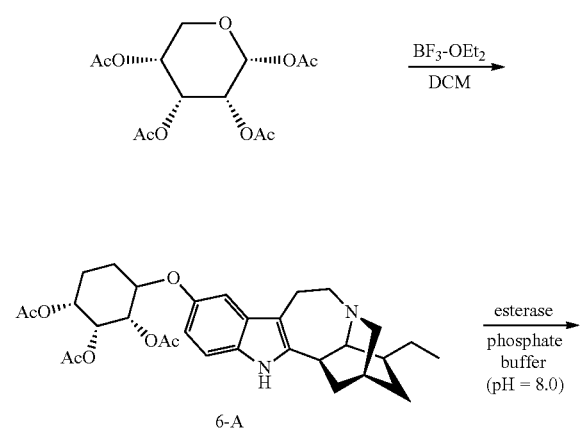

Preparation of 6-A

A mixture of noribogaine (42 mg, 0.15 mol), 1,2,3,4-tetraacetate β-D-ribopyranose (95 mg, 0.30 mmol) and 4 Å molecular sieves (2 g) in DCM (5 mL) was stirred at room temperature for 10 min. Boron trifluoride etherate complex (500 μL, 4.0 mmol) was added, and resulting mixture was stirred at the temperature for 2 h. The reaction mixture was diluted with DCM and then filtered. The filtrate was concentrated and further dried under high vacuum. The crude product was purified by flash column chromatography (Et$_3$N/1-PrOH/DCM: 1/10/200) to yield 6-A (30 mg).

MS calculated for ($C_{30}H_{38}N_2O_8$): 554; MS found (M+H): 555

Preparation of 6

Esterase (from porcine liver) suspension (1 drop) was added into a solution of the triacetate 6-A (30 mg, 0.054 mmol) in 20 mL of phosphate buffer (10 mM, pH 8.0). The reaction mixture was stirred at 25° C. for 96 h, and then treated with 20 mL of MeOH. The resulting solution was concentrated to 3 mL purified by on prep HPLC to yield 7.0 mg of the pure compound 6.

MS calculated for ($C_{24}H_{32}N_2O_5$): 428; MS found (M+H): 429. $^1$H NMR (CD$_3$OD) δ 7.18 (d, J=8.7 Hz, 1H), 7.16 (d, J=2.4 Hz, 1H), 6.87 (dd, J=8.7 and 2.1 Hz, 1H), 5.37 (d, J=3.9 Hz, 1H), 4.03 (m, 1H), 3.96-3.50 (m, 8H), 3.43-3.08 (m, 3H), 2.38-2.24 (m, 1H), 2.18-1.96 (m, 6H), 1.80-1.58 (m, 3H), 1.46-1.26 (m, 2H), 1.05 (t, J=7.5 Hz, 3H).

Example 7

Preparation of Compound 7

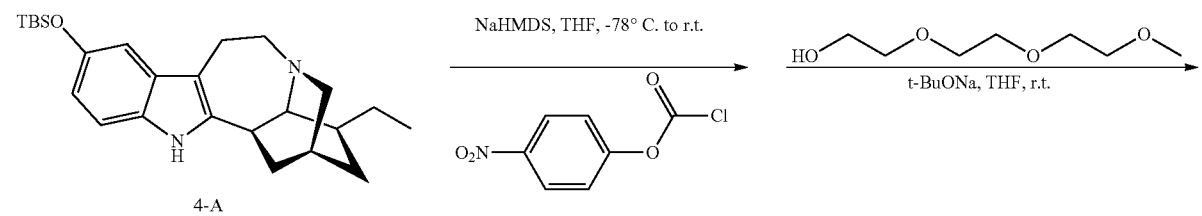

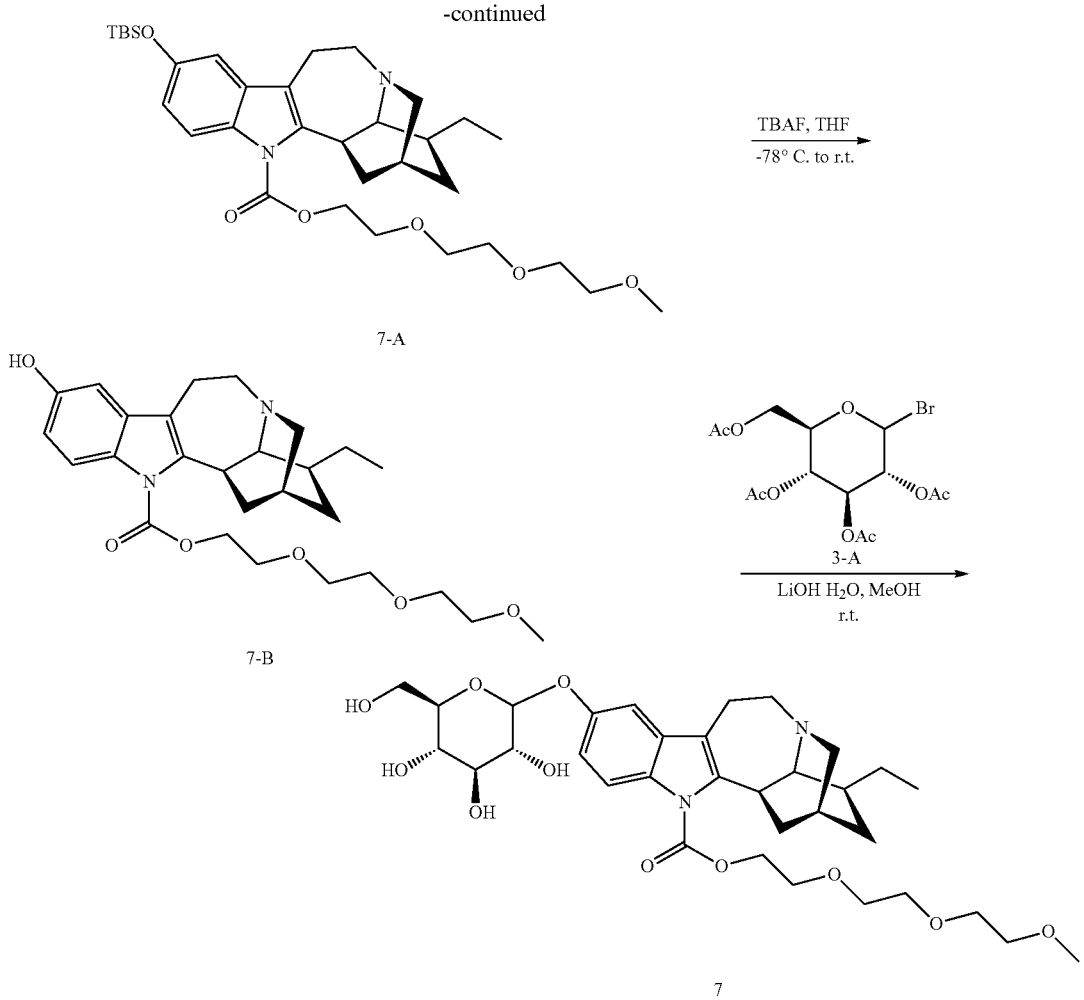

Preparation of TBS-noribogaine-PEG 7-A

NaHMDS (0.6 mL, 1.0 M solution in THF) was added into a solution of TBS-noribogaine 4-A (164 mg, 0.4 mmol) in THF (8 mL) at −78° C. The resulting solution was stirred for 10 min at −78° C. before a solution of 4-nitrophenyl chloroformate (126 mg, 0.6 mmol) in THF (6 mL, pre-cooled to −78° C.) was added quickly. The reaction mixture was warmed up to room temperature and stirred for 30 min before it was again cooled back to −78° C. NaHMDS (0.8 mL, 1.0 M solution in THF) was added to a solution of triethyleneglycol methyl ether (0.125 mL, 0.8 mmol) in THF (6 mL) at −78° C. The resulting solution was warmed up to room temperature and stirred for 10 min. This solution of deprotonated PEG alcohol was then added into the above reaction mixture at −78° C. via syringe. After stirring at room temperature for one hour, the reaction mixture was partitioned between dichloromethane and water. The layers were separated, and the aqueous phase was extracted with EtOAc. The combined organic layers were washed with brine and dried over $Na_2SO_4$. After concentration the crude product was purified by column chromatography (EtOAc/hexanes, v/v, 1/1 to pure EtOAc). The desired product 7-A (114 mg) was obtained as a yellow oil.

MS calculated for ($C_{33}H_{52}N_2O_6Si$): 600, MS found (M+1): 601.

Preparation of 7-B

TBAF (0.48 mL, 1.0 M solution in THF) was added to a solution of 7-A (114 mg, 0.19 mmol) in THF (5 mL) at −78° C. The resulting solution was stirred for 15 min at −78° C. and 40 min at room temperature before it was concentrated and purified by column chromatography (dichloromethane/2-propanol/triethylamine, v/v, 10/1/0 to 100/20/1). The resulting product was further purified by prep-HPLC to give pure 7-B (68 mg) as a slightly yellow solid.

MS calculated for ($C_{27}H_{38}N_2O_6$): 486, MS found (M+1): 487. $^1$H NMR ($CD_3CN$) δ 10.75 (bs, 1H), 8.05 (d, 1H), 7.62 (bs, 1H), 7.03 (s, 1H), 6.95 (d, 1H), 4.55-4.73 (m, 2H), 4.12 (dd, 1H), 3.86-4.06 (m, 3H), 3.48-3.85 (m, 11H), 3.36 (s, 3H), 3.05-3.25 (m, 3H), 2.63 (t, 1H), 2.20-2.45 (m, 4H), 1.90-2.20 (m, 1H), 1.76-1.95 (m, 2H), 1.54 (d, 1H), 1.02-1.18 (m, 3H).

Preparation of 7

Phenol 7-B (65 mg, 0.134 mmol), tetra-acetyl glucose bromide 3-A (110 mg, 0.267 mmol) and LiOH monohydrate (23 mg, 0.53 mmol) were dissolved in MeOH (3 mL). The solution was stirred at room temperature for one hour before more 3-A (60 mg) and LiOH monohydrate (11 mg) were added. After stirring one additional hour, the reaction was quenched by adding 1N aq. HCl (0.9 mL). Prep-HPLC purification afforded compound 7 (12.9 mg) as a white solid.

MS calculated for ($C_{33}H_{48}N_2O_{11}$): 648, MS found (M+1): 649. $^1$H NMR (CD$_3$CN) δ 8.00 (d, 0.5H), 7.92 (d, 0.5H), 7.16-7.23 (m, 1H), 7.00-7.08 (m, 1H), 4.94 (d, 1H), 4.45-4.62 (m, 1H), 3.90-4.05 (m, 2H), 3.70-3.90 (m, 3H), 3.25-3.70 (m, 22H), 3.26 (s, 3H), 3.05-3.22 (m, 3H), 2.40-2.58 (m, 1H), 2.18 (bs, 1H), 1.85-2.05 (m, 1H), 1.30-1.76 (m, 4H), 0.96 (t, 3H).

Example 8

Preparation of Compound 8

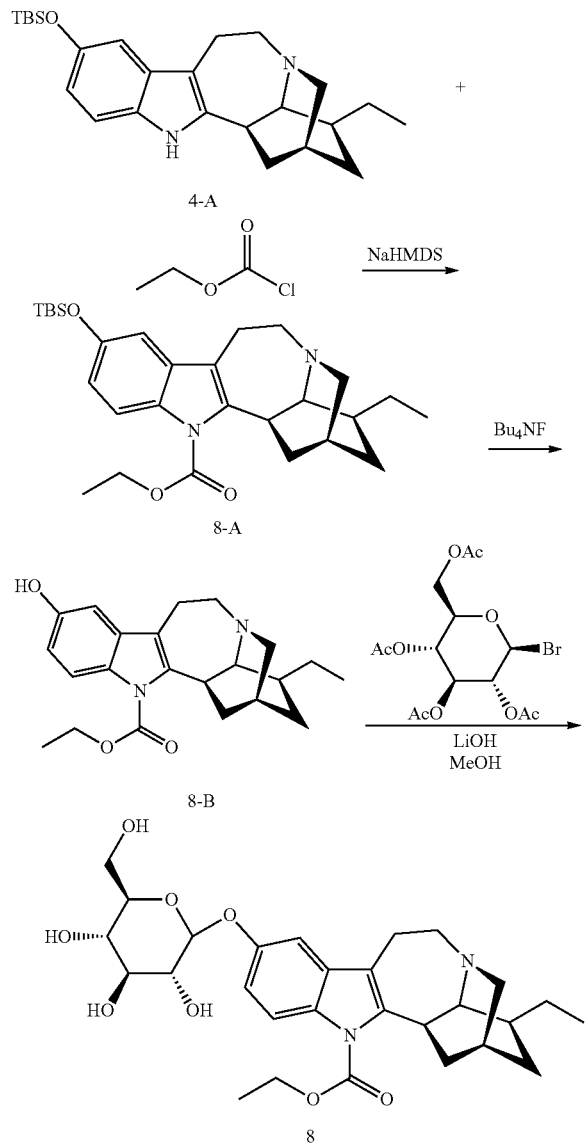

Preparation of 8-A

A solution of compound 4-A (102 mg, 0.25 mmol) in THF (3 mL) was cooled at −78° C., and then 0.38 mL of 1 N NaHMDS in THF was added. After 15 min, a solution of ethyl chloroformate (48 μL, 0.50 mmol) was added. The reaction mixture was stirred at −78° C. for 20 min, and then slowly warmed up to room temperature. The reaction was quenched with water after 2 h. The product was extracted with DCM, and the combined organic extracts were dried over MgSO$_4$. Concentration of the filtrate, finally under high vacuum afforded pure compound 8-A (120 mg).

MS calculated for ($C_{28}H_{42}N_2O_3Si$): 482, MS found (M+1): 483.

Preparation of 8-B

A solution of Bu$_4$NF in THF (1.0 M, 0.50 mL) was added into a solution of compound 8-A (0.12 mg, 0.25 mmol) in THF (5 mL) at −78° C. The resulting mixture was stirred at −78° C. for 30 min and then at room temperature for 1 h. A few drops of 1 N aq. HCl were added to quench the reaction. The reaction mixture was concentrated, and the residue was purified by chromatography on silica gel using NEt$_3$/iPrOH/DCM (2/10/200) as eluent to give compound 8-B (69 mg, 75%).

MS calculated for ($C_{22}H_{28}N_2O_3$): 368, MS found (M+1): 369.

Preparation of 8

LiOH (32 mg, 0.75 mmol) was added into a solution of 8-B (69 mg, 0.19 mmol) and 1-bromo-2,3,4,6-tetra-O-acetyl-glucopyranose (156 mg, 0.38 mmol) in MeOH (4 mL). The resulting mixture was stirred at room temperature for 1 h. The reaction was quenched by adding a few drops of 1 N aq, HCl. The crude product was purified by prep-HPLC to give compound 8 (20 mg, 20%).

MS calculated for ($C_{28}H_{38}N_2O_8$): 530, MS found (M+1): 531. $^1$H NMR (CD$_3$OD) δ 7.95 (d, J=9.0 Hz, 1H), 7.25 (d, J=2.1 Hz, 1H), 7.09 (dd, J=2.1 and 9.0 Hz, 1H), 4.49 (t, J=7.2 Hz, 2H), 4.18-4.08 (m, 1H), 3.96-3.82 (m, 3H), 3.74-3.64 (m, 1H), 3.60-3.40 (m, 5H), 3.38-3.28 (m, 3H), 3.26-3.12 (m, 3H), 2.68-2.54 (m, 1H), 2.21 (bs, 1H), 2.14-1.96 (m, 2H), 1.72-1.42 (m, 6H), 1.05 (t, J=7.2 Hz, 3H).

What is claimed is:
1. A compound of Formula I:

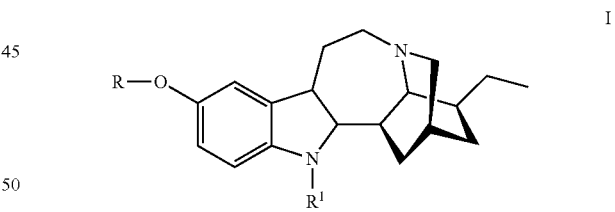

wherein
R is hydrogen, alkyl, —C(O)-alkyl, or the group -L-S where L is a covalent bond or is a biocompatible, cleavable linking group and S is a dehydrating saccharide or oligosaccharide;
R$^1$ is hydrogen or the group -L-S where L is a covalent bond or is a biocompatible, cleavable linking group and S is a dehydrating saccharide or oligosaccharide; provided that at least one of R and R$^1$ is -L-S:
or a pharmaceutically acceptable salt thereof.
2. The compound of claim 1, wherein R is hydrogen or —C(O)alkyl and R$^1$ is -L-S.
3. The compound of claim 1, wherein R is -L-S and R$^1$ is hydrogen.
4. The compound of claim 1, wherein R and R$^1$ are -L-S.

5. The compound of claim 1, wherein R is hydrogen, mannopyranose, glucopyranose, glucopyranose-O—(CH$_2$)$_9$C(O)—, ribofuranose, or ribopyranose.

6. The compound of claim 1, wherein R$^1$ is hydrogen, glucopyranose-O—(CH$_2$)$_8$C(O)—, —C(O)O(CH$_2$CH$_2$O)$_3$CH$_3$ or —CO$_2$CH$_2$CH$_3$.

7. A pharmaceutical composition comprising a pharmaceutically acceptable excipient and a therapeutically acceptable amount of a compound of claim 1.

8. The pharmaceutical composition of claim 7, wherein R is hydrogen or —C(O)alkyl and R$^1$ is -L-S.

9. The pharmaceutical composition of claim 7, wherein R is -L-S and R$^1$ is hydrogen.

10. The pharmaceutical composition of claim 7, wherein both R and R$^1$ are -L-S.

* * * * *